(12) United States Patent
Lin

(10) Patent No.: US 11,857,457 B2
(45) Date of Patent: Jan. 2, 2024

(54) DEVICE FOR ALLEVIATING OBSTRUCTIVE SLEEP APNEA

(71) Applicant: GOOD NEWS MEDICAL CO., LTD., Keelung (TW)

(72) Inventor: Chin-Chi Lin, Keelung (TW)

(73) Assignee: GOOD NEWS MEDICAL CO., LTD., Keelung (TW)

( * ) Notice: Subject to any disclaimer, the term of this patent is extended or adjusted under 35 U.S.C. 154(b) by 457 days.

(21) Appl. No.: 17/322,066

(22) Filed: May 17, 2021

(65) Prior Publication Data

US 2021/0361470 A1    Nov. 25, 2021

(30) Foreign Application Priority Data

May 21, 2020   (CN) .......................... 202010434944.5
Mar. 4, 2021    (CN) .......................... 202110237436.2

(51) Int. Cl.
*A61F 5/56*      (2006.01)
*A61M 1/00*     (2006.01)
(Continued)

(52) U.S. Cl.
CPC ............... *A61F 5/566* (2013.01); *A61M 1/73* (2021.05); *A61M 1/86* (2021.05); *A61M 1/87* (2021.05);
(Continued)

(58) Field of Classification Search
CPC ...... A61F 2005/563; A61F 5/56; A61F 5/566; A61C 7/36; A62F 7/08; A63B 71/085;
(Continued)

(56) References Cited

U.S. PATENT DOCUMENTS 4,593,686 A * 6/1986 Lloyd ..................... A61F 5/566
430/573
5,465,734 A   11/1995 Alvarez et al.
(Continued)

FOREIGN PATENT DOCUMENTS

CN    101917924 A    12/2010
CN    102133141 A     7/2011
(Continued)

*Primary Examiner* — Camtu T Nguyen
(74) *Attorney, Agent, or Firm* — MUNCY, GEISSLER, OLDS & LOWE, PC

(57) ABSTRACT

A device for alleviating obstructive sleep apnea, comprising: a base fitted and fixed to an user's head and having a passage portion; an adjustment element extending into the passage portion and undergoing relative displacement therein; a locking element disposed at the passage portion, wherein an user uses the locking element to fix the adjustment element in place to limit the relative displacement of the adjustment element; a suction member undergoing relative displacement relative to the passage portion together with the adjustment element and having a channel, wherein the channel extends into the adjustment element, undergoes relative displacement in the adjustment element, and connects to a tongue fixing portion disposed at the front end of the user's tongue; and a negative pressure source being mounted on the base and in communication with the channel, providing a negative pressure to the user's tongue in contact with the tongue fixing portion.

47 Claims, 26 Drawing Sheets

(51) Int. Cl.
*A61M 16/06* (2006.01)
*A61M 39/24* (2006.01)

(52) U.S. Cl.
CPC ........ *A61M 16/0683* (2013.01); *A61M 39/24* (2013.01); *A61M 2205/42* (2013.01); *A61M 2209/088* (2013.01); *A61M 2210/0643* (2013.01)

(58) Field of Classification Search
CPC ....... A63B 2071/086; A63B 2071/088; A61M 1/73; A61M 1/74; A61M 1/80
See application file for complete search history.

(56) References Cited

U.S. PATENT DOCUMENTS

| | | | |
|---|---|---|---|
| 5,513,986 A * | 5/1996 | Feltham | A61C 17/08 433/91 |
| 7,328,698 B2 * | 2/2008 | Scarberry | A61M 16/0493 128/200.24 |
| 7,913,692 B2 | 3/2011 | Kwok | |
| 8,347,890 B2 | 1/2013 | Li | |
| 2004/0211430 A1 | 10/2004 | Pivovarov | |
| 2006/0213516 A1 | 9/2006 | Hoffman | |
| 2011/0265801 A1 | 11/2011 | Cullen | |
| 2012/0132216 A1 | 5/2012 | Vaska | |
| 2019/0015618 A1 | 1/2019 | Chen et al. | |

FOREIGN PATENT DOCUMENTS

| | | |
|---|---|---|
| CN | 203017450 U | 6/2013 |
| CN | 103263315 A | 8/2013 |
| CN | 103961201 A | 8/2014 |
| CN | 104870040 A | 8/2015 |
| CN | 105748187 A | 7/2016 |
| CN | 106932243 A | 7/2017 |
| CN | 108742882 A | 11/2018 |
| CN | 108916946 A | 11/2018 |
| CN | 208237299 U | 12/2018 |
| CN | 110352046 A | 10/2019 |
| CN | 209800893 U | 12/2019 |
| CN | 111685645 A | 9/2020 |
| CN | 211512256 U | 9/2020 |
| CN | 112245078 A | 1/2021 |
| JP | 5847575B2 B2 | 1/2016 |
| WO | WO-2008108789 A1 | 9/2008 |
| WO | WO 2019/101213 | 5/2019 |

* cited by examiner

DEVICE FOR ALLEVIATING OBSTRUCTIVE SLEEP APNEA

BACKGROUND

1. Technical Field

The present disclosure relates to devices for alleviating obstructive sleep apnea and, more particularly, to a device for alleviating obstructive sleep apnea by pulling a user's tongue outward.

2. Description of the Related Art

Obstructive sleep apnea, a common sleep disorder, is especially associated with the supine sleeping position, as the tongue and soft palate relax to block the airway temporarily, thereby cutting off breathing for brief periods of time. In the presence of gravity and floppy tissue, the tongue falls backward, and the soft palate collapses, leading to blockage of the upper airway. Blockage of the upper airway during sleep causes dyspnea and snoring and may even be life-threatening.

Conventional treatments for obstructive sleep apnea include pulling the tongue under an external force to keep the tongue away from the collapse position. One of the pulling solutions entails immobilizing patients' tongues with applying a negative pressure and then pulling the tongues outward. This solution has drawbacks described below. Related constituent components are manufactured by batch production, and thus the course of pulling the patients' tongues is not adjustable. The shape and size of the upper airway and the severity of symptoms varies from patient to patient, and thus the nonadjustable pulling course is not necessarily suitable for all patients, for example, overdone and irritating to some patients, but insufficient to separate the tongue completely from the collapse position in the case of the other patients. Admittedly, the aforesaid drawbacks can be overcome by customization, albeit at higher cost.

The aforesaid conventional pulling solution, which is carried out under a negative pressure, has a further drawback. A negative pressure source needs to be placed on the bedside of the patient, and a sufficiently long tube is required that connects the patient and the negative pressure source. The odds are that the patient may press, entangle or stretch the long tube unknowingly while sleeping, causing interruptions or abatement of the negative pressure to the detriment of efficacy.

Therefore, it is necessary to provide a device for alleviating obstructive sleep apnea with a view to overcoming the aforesaid drawbacks of the prior art.

SUMMARY

In order to overcome the aforesaid drawbacks of the prior art, the present disclosure provides a device for alleviating obstructive sleep apnea by pulling an user's tongue outward under a negative pressure. The course of pulling the user's tongue is adjustable. Upon completion of the adjustment, the course of pulling the user's tongue is fixed with a locking element. The device, including a negative pressure source, is worn on the user's head.

In order to achieve the above and other objectives, the present disclosure puts forth a technical solution described below.

A device for alleviating obstructive sleep apnea, comprising: a base fitted and fixed to an user's head and having a passage portion; an adjustment element extending into the passage portion and undergoing relative displacement therein; a locking element disposed at the passage portion, wherein the locking element fixes the adjustment element in place to limit the relative displacement of the adjustment element; a suction member undergoing relative displacement relative to the passage portion together with the adjustment element and having a channel, wherein the channel extends into the adjustment element, undergoes relative displacement in the adjustment element, and connects to a tongue fixing portion disposed at the front end of the user's tongue; and a negative pressure source in communication with the channel, providing a negative pressure to the user's tongue in contact with the tongue fixing portion, being an electrical module comprising a negative pressure pump and a power source, and being mounted on the base, wherein the channel is in communication with the negative pressure pump.

Furthermore, the passage portion extends in a front-rear direction, and the adjustment element undergoes forward and rearward displacement along the passage portion. The locking element has a locking portion. The locking portion protrudes in a first direction perpendicular to the front-rear direction and thus is inserted into the passage portion to lock the adjustment element, thereby limiting displacement of the adjustment element in the front-rear direction.

Furthermore, an outer surface of the adjustment element dents inward to form a positioning slot, and the locking portion enters the positioning slot to stop the adjustment element from undergoing displacement in the front-rear direction.

Furthermore, the locking element has a retaining portion and a resilient arm. The retaining portion is fixed to the base. The resilient arm is movable relative to the retaining portion in the first direction and has the locking portion.

Furthermore, the resilient arm has an unlocking-facilitating portion. The unlocking-facilitating portion operates in conjunction with a driving element. One of the unlocking-facilitating portion and the driving element has an unlocking groove, and the other one has an unlocking protruding portion. The unlocking protruding portion is received in the unlocking groove. The driving element has a pressing portion positioned behind the unlocking-facilitating portion. The pressing portion protrudes in a direction away from the outer surface of the passage portion. When the pressing portion is pressed, causing the driving element to drive the locking portion to separate from the positioning slot.

Furthermore, the retaining portion comprises a plurality of snap-engagement arms spaced apart from each other and extending forward and rearward. The rear end of each snap-engagement arm has a snap-engagement bump, allowing the snap-engagement bump and the base to be snap-engaged with each other.

Furthermore, the passage portion has a slot receiving the locking element, penetrating the passage portion outward in the first direction, and having a limiting segment corresponding in position to the resilient arm. The limiting segment confines the resilient arm to the first direction, and the least dimension of the limiting segment in a second direction is less than the greatest dimension of the resilient arm in the second direction. The second direction is perpendicular to the first direction and the front-rear direction.

Furthermore, the outer surface of the adjustment element and an inner surface of the passage portion have threads operating in conjunction with each other and allowing the adjustment element to rotate and thereby undergo forward and rearward displacement, and the positioning slot is disposed on a threaded area of the outer surface of the adjustment element. The locking portion enters the positioning slot to stop the rotation of the adjustment element.

Furthermore, the positioning slot extends linearly in the front-rear direction.

Furthermore, the suction member has a stopping portion operating in conjunction with the adjustment element and adapted to limit forward displacement of the tongue fixing portion.

Furthermore, the suction member has a connector connected to another end of the channel relative to the tongue fixing portion and in communication with the negative pressure source and the channel. The stopping portion is disposed at the connector.

Furthermore, the negative pressure source is in communication with the connector via a catheter, and two ends of the connector each have a hermetic seal element. The two hermetic seal elements fit around the channel and the catheter, respectively, to press the channel and the catheter against the connector tightly. The stopping portion is disposed at one of the hermetic seal elements.

Furthermore, the connector comprises an axle portion and two mouths disposed at a front end and a rear end of the axle portion, respectively. The hermetic seal elements are connected to the axle portion by the threads, one of the two mouths is inserted into the catheter, and the one of the two mouths is inserted to the channel. An outer surface of each said mouth has a convex portion protruding outward radially and surrounding the mouth to widen the catheter fitting around one of the two mouths and widen the channel fitting around the other one of the two mouths. One of the widened catheter and the widened channel is clamped radially by a corresponding one of the convex portions and a corresponding one of the hermetic seal elements.

Furthermore, the device further comprises a resilient element for providing an elastic force under which the tongue fixing portion approaches the base. The elastic force is not only weaker than a suction force between the suction member and the user's tongue but also weaker than a pulling force exerted by the user's tongue by muscular activity.

Furthermore, the adjustment element comprises a front lid which the suction member abuts against and a cylinder meshing with the front lid, wherein the resilient element is a spring received in the cylinder, has an end abutting against a rear end of the cylinder, and has another end abutting against the suction member, such that the extent to which the resilient element is compressed or extended is adjusted through forward and rearward displacement of the front lid relative to the cylinder.

Furthermore, the negative pressure source comprises a casing for receiving the negative pressure pump and the power source, and the casing has a through hole for receiving the passage portion.

Furthermore, a rail comprising a guiding groove and a fixing recess is concavely disposed on one of an outer surface of the passage portion and an inner surface of the through hole, and the other one has a positioning protruding portion operating in conjunction with the rail, wherein the guiding groove extends forward, and the fixing recess extends, such that an included angle is formed between the direction in which the guiding groove extends and the direction in which the fixing recess extends, wherein the passage portion and the casing are combined by moving the positioning protruding portion along the guiding groove and then along the fixing recess before fixing the positioning protruding portion to the fixing recess.

Furthermore, the fixing recess comprises a fixing segment extending forward or rearward, and the rail further comprises an engaging member, wherein, when the casing and the base are fixed to each other, the positioning protruding portion is positioned at the fixing segment to block the engaging member and thereby prevent the positioning protruding portion from separating from the fixing recess and consequently entering the guiding groove.

Furthermore, the device further has an operating element disposed between the casing and the base to enable the casing to be moved in the front-rear direction relative to the base, thereby allowing the casing to be firmly fixed in place.

Furthermore, the operating element is a resilient rubber ring compressed by the casing and the base because of movement of the positioning protruding portion along the guiding groove, wherein, upon admittance of the positioning protruding portion to the fixing recess, both the casing and the base move in the front-rear direction under a resilient force of the operating element, and thus the positioning protruding portion enters the fixing segment.

Furthermore, the casing comprises a front case and a rear case which are combined, and the rail is formed on the front case and the rear case and concavely disposed on an inner surface of the through hole, wherein the fixing segment and the engaging member are disposed on the rear case, and the remainder of the fixing recess is disposed on the front case.

Furthermore, the tongue fixing portion at least encloses a front end of the user's tongue, and a thickened portion is protrudingly disposed on each of upper and lower outer surfaces of the tongue fixing portion to hold the user's teeth.

Furthermore, the thickened portion at the upper outer surface and the thickened portion at the lower outer surface have an oblique surface, respectively, wherein the oblique surface at the upper outer surface and the oblique surface at the lower outer surface approach each other in the upward and downward directions at a front end of the tongue fixing portion, wherein, when the user's upper and lower teeth come into contact with the thickened portions, the upper teeth and the lower teeth approach each other along the oblique surfaces at the upper and lower outer surfaces, and the thickened portions move rearward relative to the user's teeth, thereby driving the tongue fixing portion and the user's tongue to move rearward relative to the user's teeth.

Furthermore, the base comprises a mask portion whereby the user wears the device, and a gap is disposed between the mask portion and the negative pressure source, wherein the mask portion further has a plurality of ventilation pores in communication with the gap.

Furthermore, a negative pressure sensor and a check valve are disposed between the negative pressure pump and the tongue fixing portion, and the check valve is disposed between the negative pressure sensor and the negative pressure pump, wherein the negative pressure sensor measures magnitude of negative pressure between the check valve and the tongue fixing portion, and the device controls the negative pressure pump according to a measurement, wherein the check valve only permits gas to flow unidirectionally from the tongue fixing portion to the negative pressure pump, such that negative pressure leaking from the negative pressure pump is prevented from transmitting to the negative pressure sensor and the tongue fixing portion.

Furthermore, the locking element is a screw, and the base has a threaded hole for meshing with the locking element.

Furthermore, the negative pressure source further comprises an active noise-attenuating unit, a negative pressure sensor and a controller. The active noise-attenuating unit attenuates the noise generated by the negative pressure pump. The negative pressure sensor monitors the magnitude of negative pressure generated by the negative pressure pump. The controller starts or shuts down the active noise-attenuating unit and the negative pressure pump simultaneously according to a negative pressure measurement provided by the negative pressure sensor.

Furthermore, the active noise-attenuating unit has a built-in noise model corresponding to the negative pressure pump, such that the active noise-attenuating unit generates a first noise-attenuated sound wave with a phase inverse to the built-in noise model when the negative pressure pump starts, wherein after a sound wave resulting from superposition of actual noise generated by the negative pressure pump and the first noise-attenuated sound wave has been received by the active noise-attenuating unit, the active noise-attenuating unit generates a second noise-attenuated sound wave with a phase inverse to the sound wave actually received.

Furthermore, the negative pressure source comprises a controller, and the power source is a rechargeable battery. After receiving a signal which indicates that the power source is being recharged, the controller causes the negative pressure pump to stop functioning.

Compared with the prior art, the present disclosure has advantages described below. The user plays an active role in operating the adjustment element, such that the suction member undergoes relative displacement relative to the passage portion together with the adjustment element to thereby alter the course of pulling the user's tongue, thereby minimizing the user's discomfort while the user is receiving therapy for obstructive sleep apnea. Since the course of the movement of the adjustment element is fixed with the locking element, the adjustment element in use cannot be loosened but can be reused repeatedly and conveniently. The negative pressure source is mounted on the base; thus, the device, including the negative pressure source, can be worn on the user's head to thereby not only shorten the required length of a tube connecting the patient and the negative pressure source but also prevent the tube from being pressed, entangled or stretched. Furthermore, with the tube being short, the operating power of the negative pressure source and thus the noise and weight of the negative pressure source can be minimized.

In view of the aforesaid drawbacks of the prior art, it is an objective of the present disclosure to provide a device for pulling an user's tongue outward under a negative pressure in such a manner that the course of pulling the user's tongue can be freely adjusted.

In order to achieve the above and other objectives, the present disclosure puts forth a technical solution described below.

A device for alleviating obstructive sleep apnea, comprising: a base fitted and fixed to an user's head and having a passage portion; an adjustment element extending into the passage portion and undergoing relative displacement therein; a suction member undergoing relative displacement relative to the passage portion together with the adjustment element and having a channel, wherein the channel extends into the adjustment element, undergoes relative displacement in the adjustment element, and connects to a tongue fixing portion disposed at the front end of the user's tongue; and a negative pressure source in communication with the channel and providing a negative pressure to the user's tongue in contact with the tongue fixing portion.

Furthermore, the base further comprises a locking element, and the locking element fixes the adjustment element in place to limit the relative displacement of the adjustment element.

Furthermore, the passage portion extends in a front-rear direction, and the adjustment element undergoes forward and rearward displacement along the passage portion, with the locking element having a locking portion, wherein the locking portion protrudes in a first direction perpendicular to the front-rear direction and thus is inserted into the passage portion to lock the adjustment element, thereby limiting forward and rearward displacement of the adjustment element.

Furthermore, an outer surface of the adjustment element dents inward to form a positioning slot, and the locking portion enters the positioning slot to stop forward and rearward displacement of the adjustment element.

Furthermore, the locking element has a retaining portion and a resilient arm, with the retaining portion fixed to the base, wherein the resilient arm is movable relative to the retaining portion in the first direction and has the locking portion.

Furthermore, the resilient arm has an unlocking-facilitating portion operating in conjunction with a driving element, wherein one of the unlocking-facilitating portion and the driving element has an unlocking groove, and the other one has an unlocking protruding portion received in the unlocking groove, wherein the driving element has a pressing portion positioned behind the unlocking-facilitating portion and protruding in a direction away from an outer surface of the passage portion, wherein, when the pressing portion is pressed, causing the driving element to drive the locking portion to separate from the positioning slot.

Furthermore, the retaining portion comprises a plurality of snap-engagement arms spaced apart from each other and extending forward and rearward, wherein a rear end of each said snap-engagement arm has a snap-engagement bump, allowing the snap-engagement bump and the base to be snap-engaged with each other.

Furthermore, the passage portion has a slot receiving the locking element, penetrating the passage portion outward in the first direction, and having a limiting segment corresponding in position to the resilient arm, wherein the limiting segment confines the resilient arm to the first direction, and the least dimension of the limiting segment in a second direction is less than the greatest dimension of the resilient arm in the second direction. The second direction is perpendicular to the first direction and the front-rear direction.

Furthermore, the outer surface of the adjustment element and an inner surface of the passage portion have threads operating in conjunction with each other and allowing the adjustment element to rotate and thereby undergo forward and rearward displacement, and the positioning slot is disposed on a threaded area of the outer surface of the adjustment element.

Furthermore, the positioning slot extends linearly in the front-rear direction.

Furthermore, the locking element is a screw, and the base has a threaded hole for meshing with the locking element.

Furthermore, the negative pressure source comprises a casing with a through hole for receiving the passage portion, and a positioning protruding portion is protrudingly disposed on an outer surface of the passage portion, wherein a rail is concavely disposed on an inner surface of the through hole and comprises a guiding groove and a fixing recess, the guiding groove extending forward, and the fixing recess extending from the guiding groove in a circumferential direction of the through hole, wherein the passage portion and the casing are combined by moving the positioning protruding portion along the guiding groove and then along the fixing recess before fixing the positioning protruding portion to the fixing recess.

Furthermore, the fixing recess has a fixing segment extending rearward, and the positioning protruding portion is positioned at the fixing segment when the casing and the base are fixed to each other.

Furthermore, the device further comprises an operating element disposed between the casing and the base and adapted to move the casing forward relative to the base, thereby allowing the positioning protruding portion to enter the fixing segment.

Furthermore, the negative pressure source is mounted on the base, is an electrical module, and comprises a negative pressure pump and a power source, wherein the channel is in communication with the negative pressure pump.

Furthermore, the suction member has a stopping portion operating in conjunction with the adjustment element to limit forward displacement of the tongue fixing portion.

Furthermore, the device further comprises a resilient element for providing an elastic force under which the tongue fixing portion approaches the base, wherein the elastic force is less than an attractive force between the suction member and the user's tongue and less than a pulling force exerted by the user's tongue during muscular activity thereof.

Furthermore, the adjustment element comprises a front lid which the suction member abuts against and a cylinder meshing with the front lid, wherein the resilient element is a spring received in the cylinder, has an end abutting against a rear end of the cylinder, and has another end abutting against the suction member, such that the extent to which the resilient element is compressed or extended is adjusted through forward and rearward displacement of the front lid relative to the cylinder.

Compared with the prior art, the present disclosure has advantages described below. The user plays an active role in operating the adjustment element, such that the suction member undergoes relative displacement relative to the passage portion together with the adjustment element to thereby alter the course of pulling the user's tongue, thereby minimizing the user's discomfort while the user is receiving therapy for obstructive sleep apnea.

DETAILED DESCRIPTION OF THE EMBODIMENTS

Figure 1:
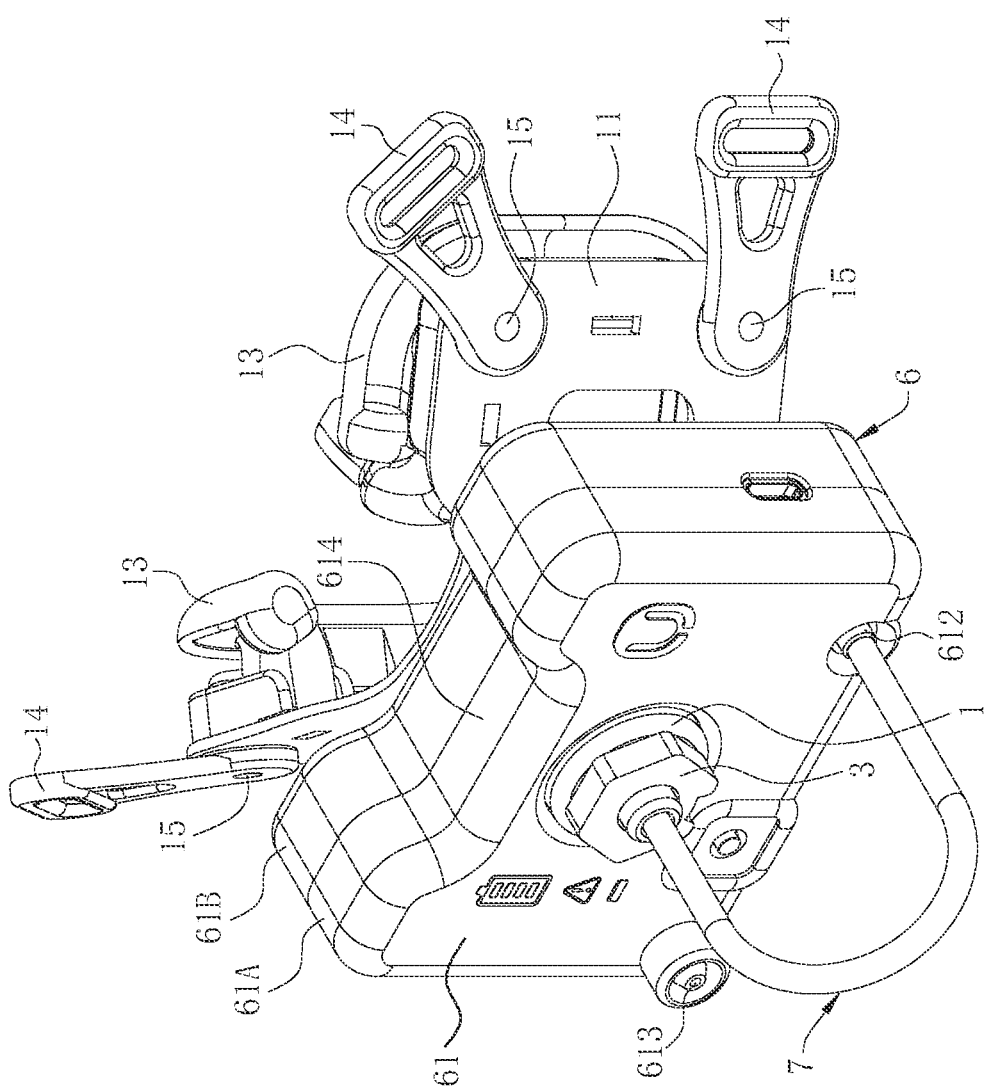
FIG. 1 is a perspective view of a device for alleviating obstructive sleep apnea according to the first embodiment of the present disclosure.

Objectives, structures, features, and advantages of the present disclosure are hereunder illustrated with specific embodiments, depicted with accompanying drawings, and described below.

Referring to FIG. 1 through FIG. 22, a device for alleviating obstructive sleep apnea, which is provided in an embodiment of the present disclosure, essentially comprises a base 1 fitted and fixed to an user's head, an adjustment element 3 movable relative to the base 1, a locking element 2 capable of limiting the movement of the adjustment element 3, a resilient element 4 received in the adjustment element 3, a suction member 5 operating in conjunction with the user's tongue T, and a negative pressure source 6 for providing a negative-pressure attractive force to the suction member 5.

Figure 2:
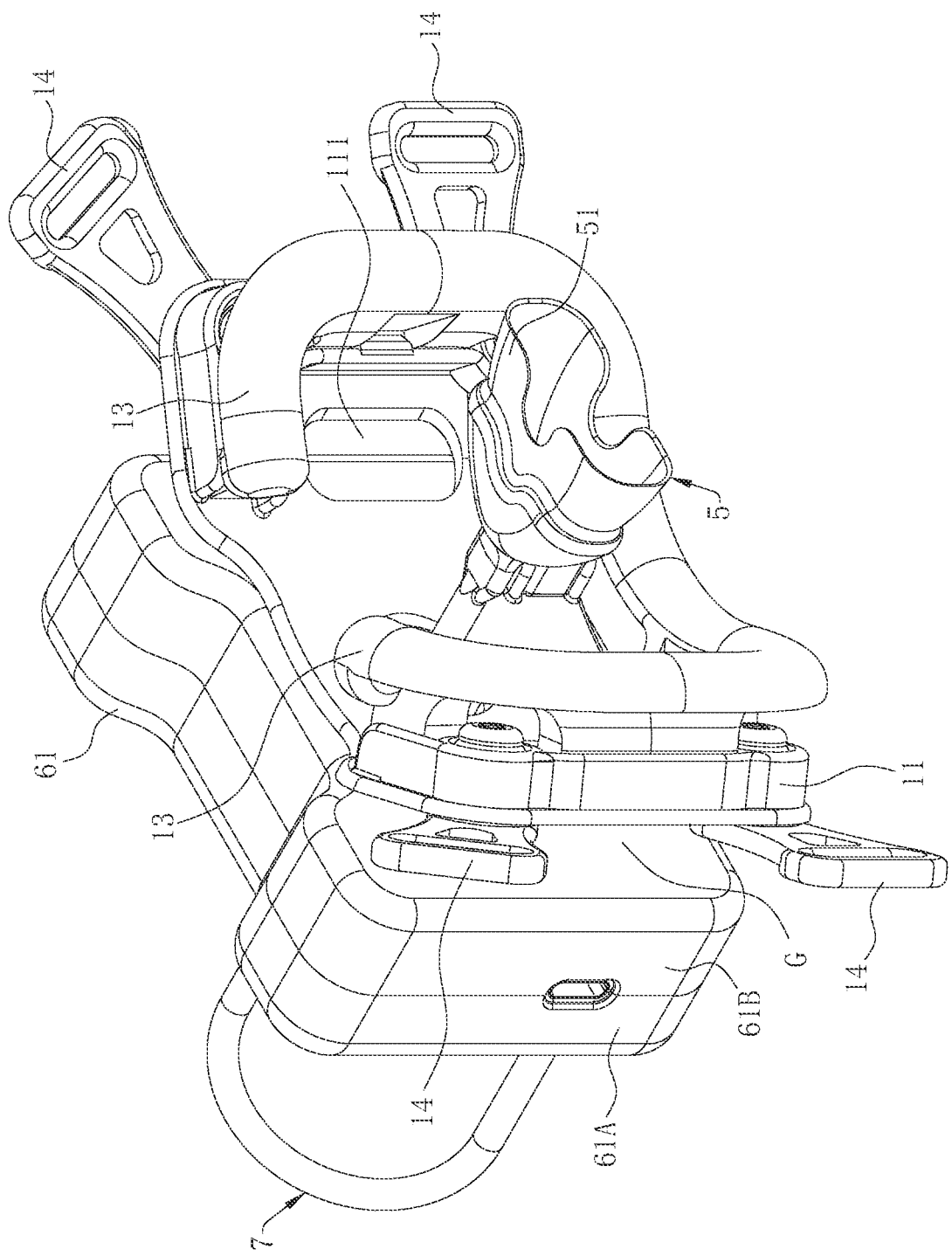
FIG. 2 is a perspective view based on FIG. 1 but rotated horizontally by 90 degrees.
Figure 3:
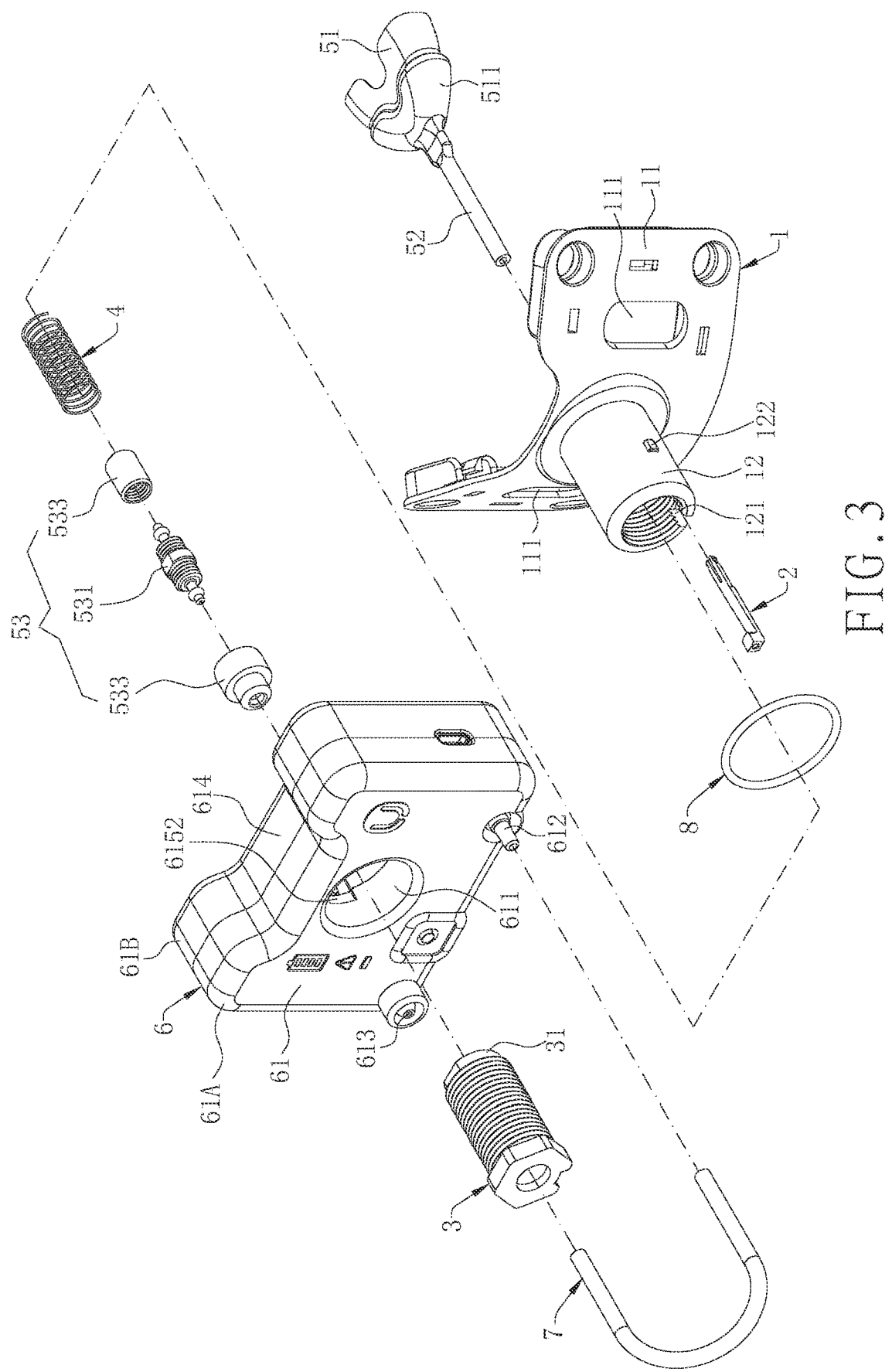
FIG. 3 is an exploded view based on FIG. 1.
Figure 26:
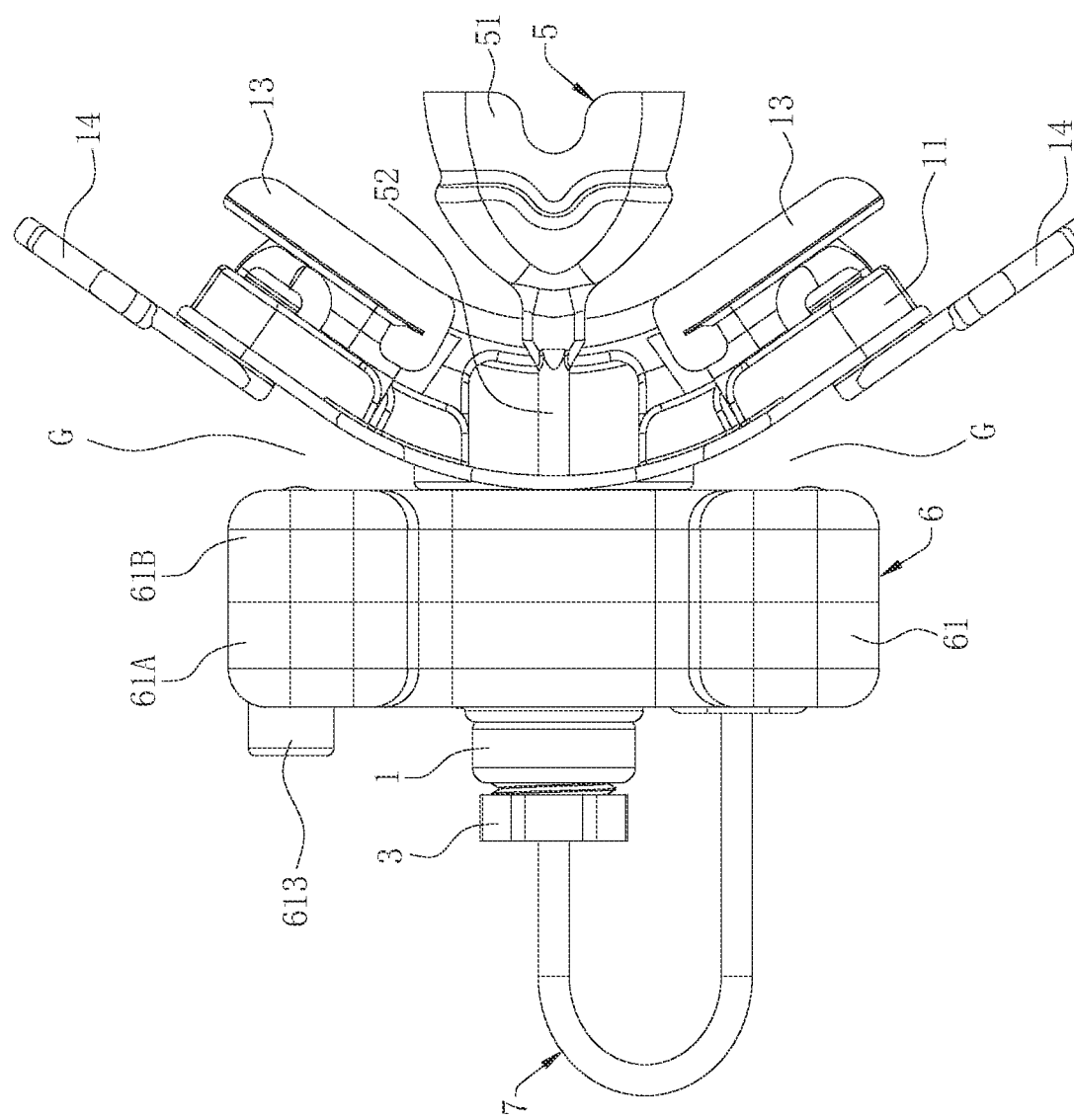
FIG. 26 is a top view based on FIG. 1.

Referring to FIG. 1 through FIG. 3, the base 1 comprises a mask-shaped mask portion 11 and a passage portion 12 protruding forward from the mask portion 11. The mask portion 11 is arcuate in order to cover the user's face. A gap G is formed between the arcuate mask portion 11 and the negative pressure source 6 in the front-rear direction. The gap G opens outward in a direction perpendicular to the front-rear direction (as shown in FIG. 26). The mask portion 11 has a pad 13 facing the user's face to increase the user's comfort while wearing the device. The pad 13 is made of a conventional, soft material, such as sponge and silicone. The mask portion 11 further has a plurality of ventilation pores 111 which are in communication with the gap G and the user's oral cavity. The ventilation pores 111 ensure that the mask portion 11 cannot hermetically seal the user's oral cavity.

Referring to FIG. 1, FIG. 2 and FIG. 3, the base 1 further comprises a plurality of connection elements 14 and a plurality of fastening elements 15. The connection elements 14 are disposed at four corners of the mask portion 11, respectively. One end of each connection element 14 and one of the fastening elements 15 mesh with each other and thus are fixed to each other; hence, the connection elements 14 are connected to the mask portion 11, and the connection elements 14 are rotatable relative to the mask portion 11. The other end of each connection element 14 is connected to straps (not shown), fixing the base 1 to the user's head.

Figure 4:
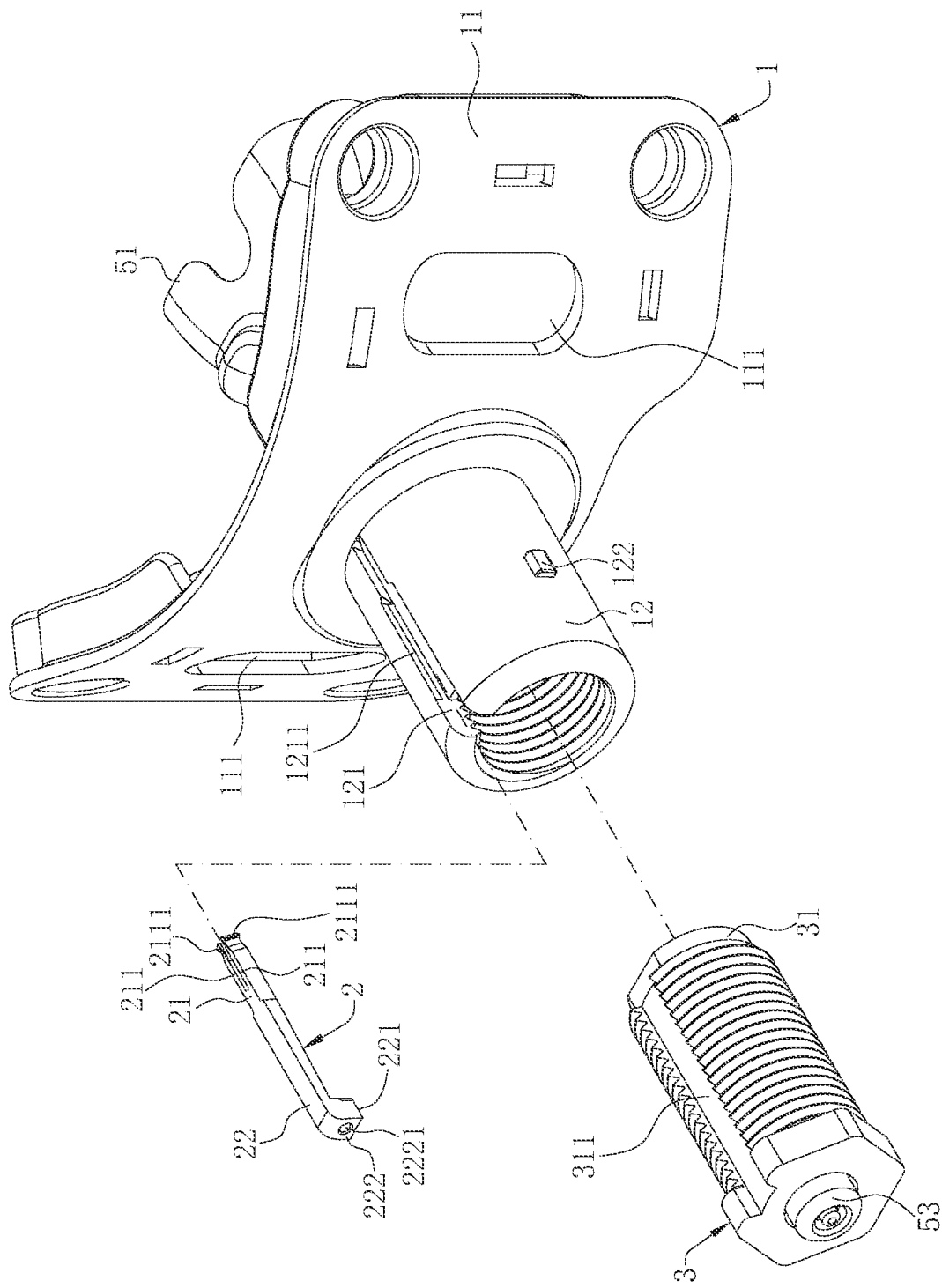
FIG. 4 is a partial exploded view of the device, omitting a negative pressure source shown in FIG. 1.
Figure 5:
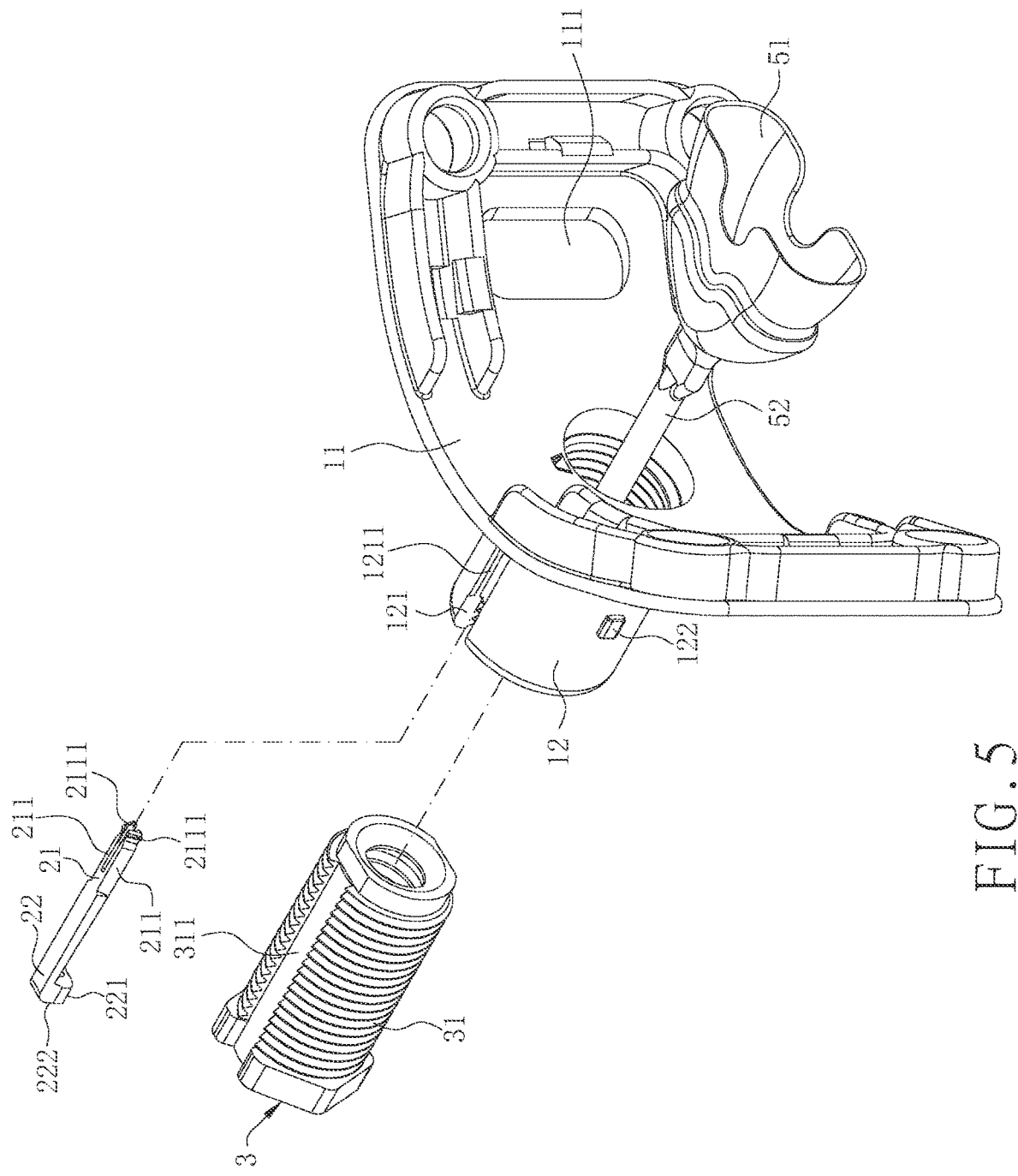
FIG. 5 is a schematic view based on FIG. 4 but rotated horizontally by 90 degrees.
Figure 6:
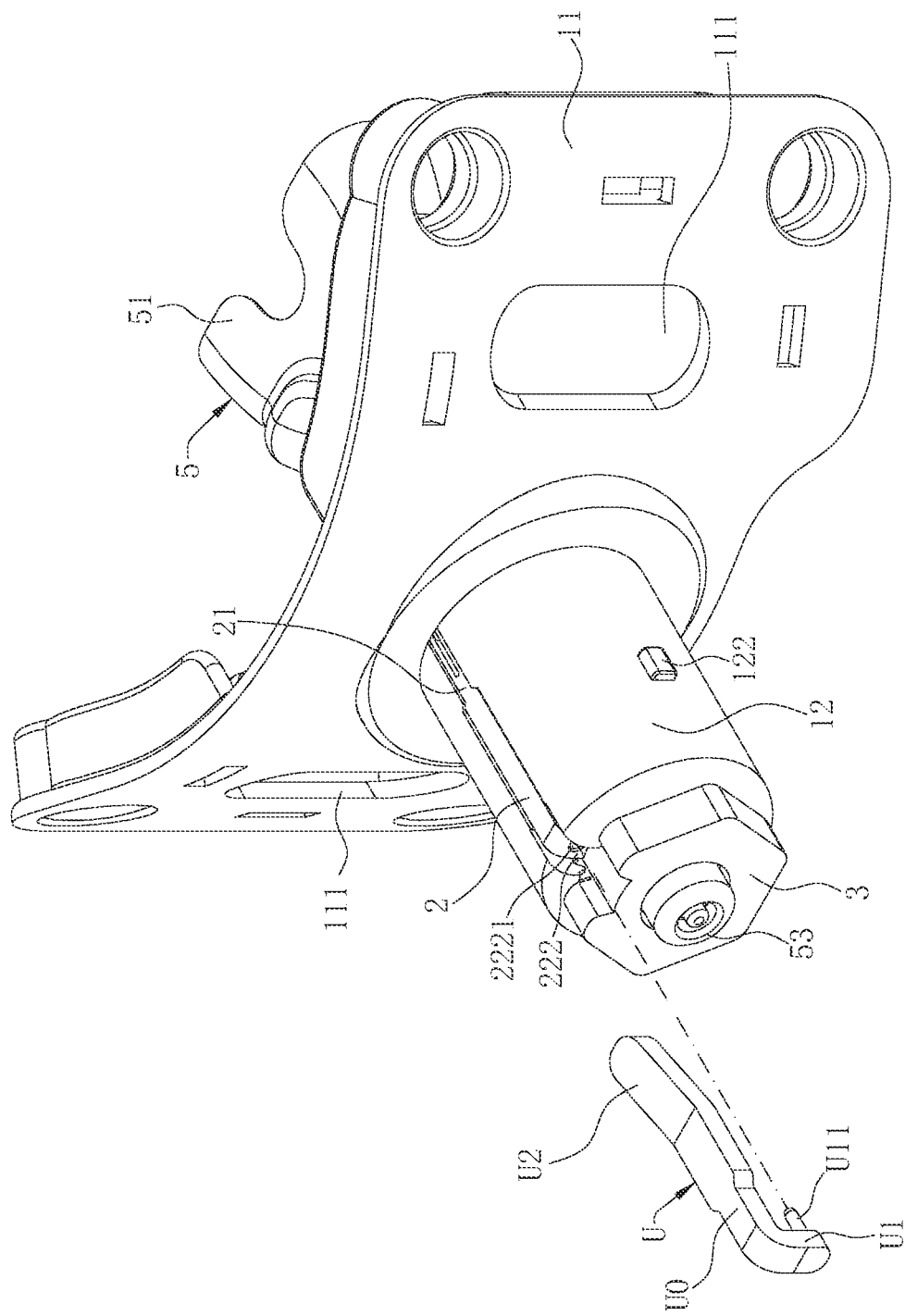
FIG. 6 is a perspective view based on FIG. 4, showing the device is assembled, but a locking element and a driving element not operating in conjunction with each other.
Figure 7:
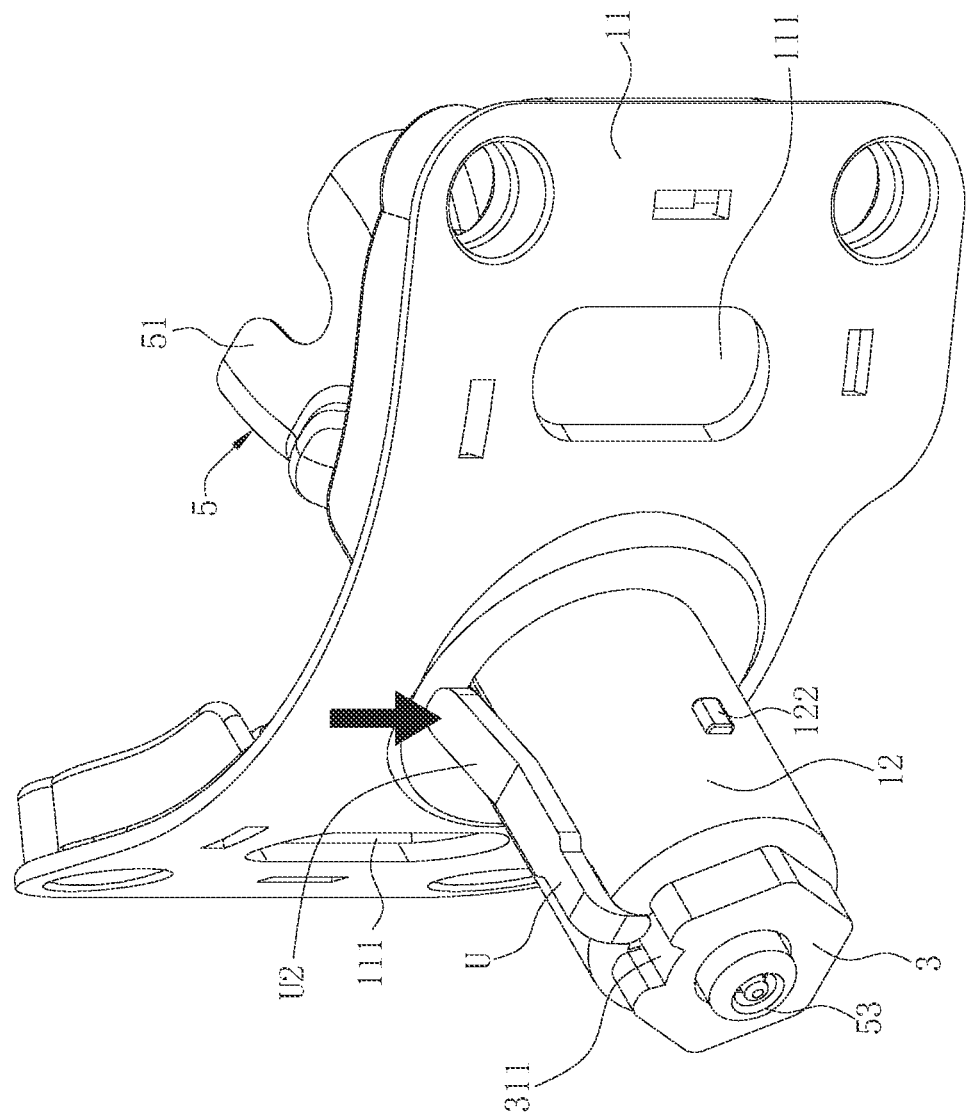
FIG. 7 is a perspective view based on FIG. 6, showing the locking element and the driving element operating in conjunction with each other.

Referring to FIG. 3 through FIG. 5, the passage portion 12 is cylindrical and extends in the front-rear direction, and it is hollow-cored to thereby receive the adjustment element 3. The threaded inner surface of the passage portion 12 meshes with the threaded outer surface of the adjustment element 3. The outer surface of the passage portion 12 dents inward to form a slot 121. The slot 121 extends in the front-rear direction to thereby receive the locking element 2. The front end of the slot 121 opens in a first direction, i.e., a radial direction of the passage portion 12 (i.e., upward and downward directions in this embodiment), so as to be in communication with the internal space of the passage portion 12. The rear end of the slot 121 extends rearward to thereby penetrate the mask portion 11. The middle part of the slot 121 is defined as a limiting segment 1211 for preventing complete separation of the locking element 2 from the passage portion 12. The two lateral sidewalls of the limiting segment 1211 are oblique relative to the first direction and approach each other in the upward direction. In this embodiment, a second direction is defined as the left-right direction and is perpendicular to the first direction and the front-rear direction. In this embodiment, two positioning protruding portions 122 are protrudingly disposed on the outer surface of the passage portion 12 to operate in conjunction with the negative pressure source 6 during the assembly process. The two positioning protruding portions 122 are disposed on the left and right sides of the passage portion 12.

Figure 8:
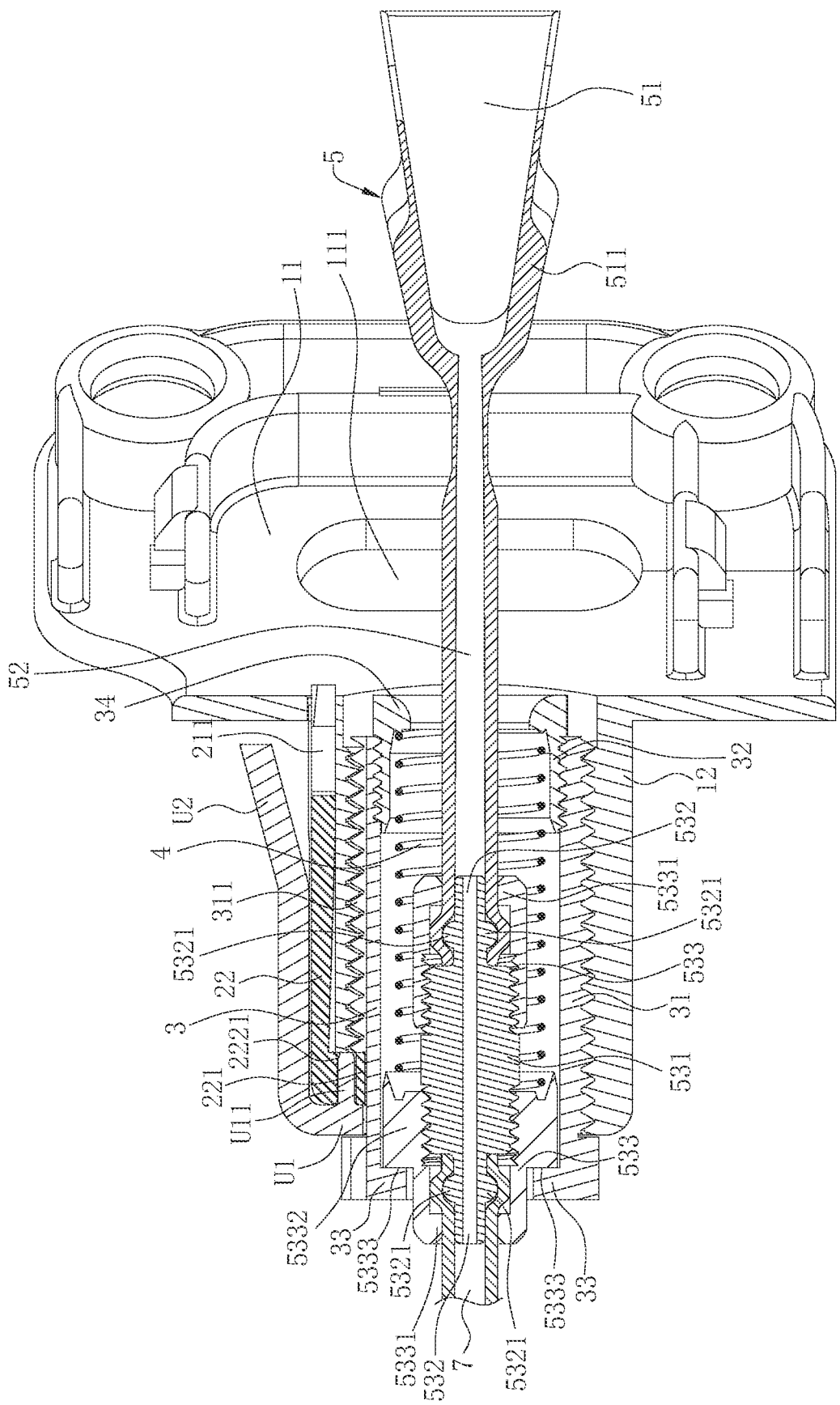
FIG. 8 is a cross-sectional view taken along the front-rear direction of FIG. 7.

Referring to FIG. 4 and FIG. 5, the locking element 2 enters the slot 121 from the front end of the passage portion 12. The locking element 2 comprises a retaining portion 21 fixed to the base 1 and a resilient arm 22 for locking the adjustment element 3. The retaining portion 21 is behind the locking element 2. In this embodiment, the front end of the retaining portion 21 operates in conjunction with and interferes with two opposing sidewalls of the slot 121, whereas the rear end of the retaining portion 21 comprises two snap-engagement arms 211. Each snap-engagement arm 211 is resilient and is terminally provided with a snap-engagement bump 2111 which protrudes in a direction perpendicular to the front-rear direction. The snap-engagement arms 211 protrude rearward beyond the slot 121. The snap-engagement bumps 2111 are snap-engaged with the rear surface (facing the user's face) of the mask portion 11. The resilient arm 22 is connected to the front end of the retaining portion 21. A locking portion 221 protrudes from the front end of the resilient arm 22 and protrudes in the first direction toward the interior of the passage portion 12 to consequently enter the passage portion 12, so as to stop the displacement of the adjustment element 3. The resilient arm 22 swings in its entirety in the first direction. In the first direction, the resilient arm 22 has a thin portion proximate to the locking portion 221 and a thick portion proximate to the retaining portion 21 (as shown in FIG. 8). The thin portion of the resilient arm 22 can bend readily, such that the locking portion 221 can separate from the adjustment element 3 in the first direction to unlock the adjustment element 3.

Referring to FIG. 6 through FIG. 9, the resilient arm 22 has an unlocking-facilitating portion 222 which matches a driving element U. In this embodiment, the locking element 2 uses the driving element U to effectuate unlocking. The unlocking-facilitating portion 222 has an unlocking groove 2221 formed by denting the front end surface of the resilient arm 22 in a rearward direction. The driving element U comprises a body portion U0 extending straightly, an unlocking portion U1 bending downward from the front end of the body portion U0, and a pressing portion U2 bending upward from the rear end of the body portion U0. The unlocking portion U1 has an unlocking protruding portion U11 which protrudes rearward and operates in conjunction with the unlocking-facilitating portion 222. To unlock the locking element 2 with the driving element U, an operator (such as, patients, family members or medical personnel, etc.) mounts the driving element U on the unlocking-facilitating portion 222 from behind to cause the unlocking protruding portion U11 to enter the unlocking groove 2221, has the connection between the body portion U0 and the pressing portion U2 pressed against the outer surface of the passage portion 12 to function as a fulcrum, such that the pressing portion U2 protrudes outward relative to the outer surface of the passage portion 12, and presses the pressing portion U2 to cause the driving element U to rotate about the fulcrum, causing the unlocking portion U1 to bend upward and thereby driving the locking portion 221 to separate from the adjustment element 3 in the first direction. After the locking element 2 has been unlocked, the adjustment element 3 undergoes forward and rearward displacement relative to the base 1. When the operator stops pressing the pressing portion U2, the resilient arm 22 relies on its own resilience to restore its initial position and drive the locking portion 221 into the slot 121, thereby locking the adjustment element 3 anew. In another embodiment, the unlocking protruding portion U11 is disposed on the unlocking-facilitating portion 222, and the unlocking groove 2221 is disposed on the unlocking portion U1.

Figure 10:
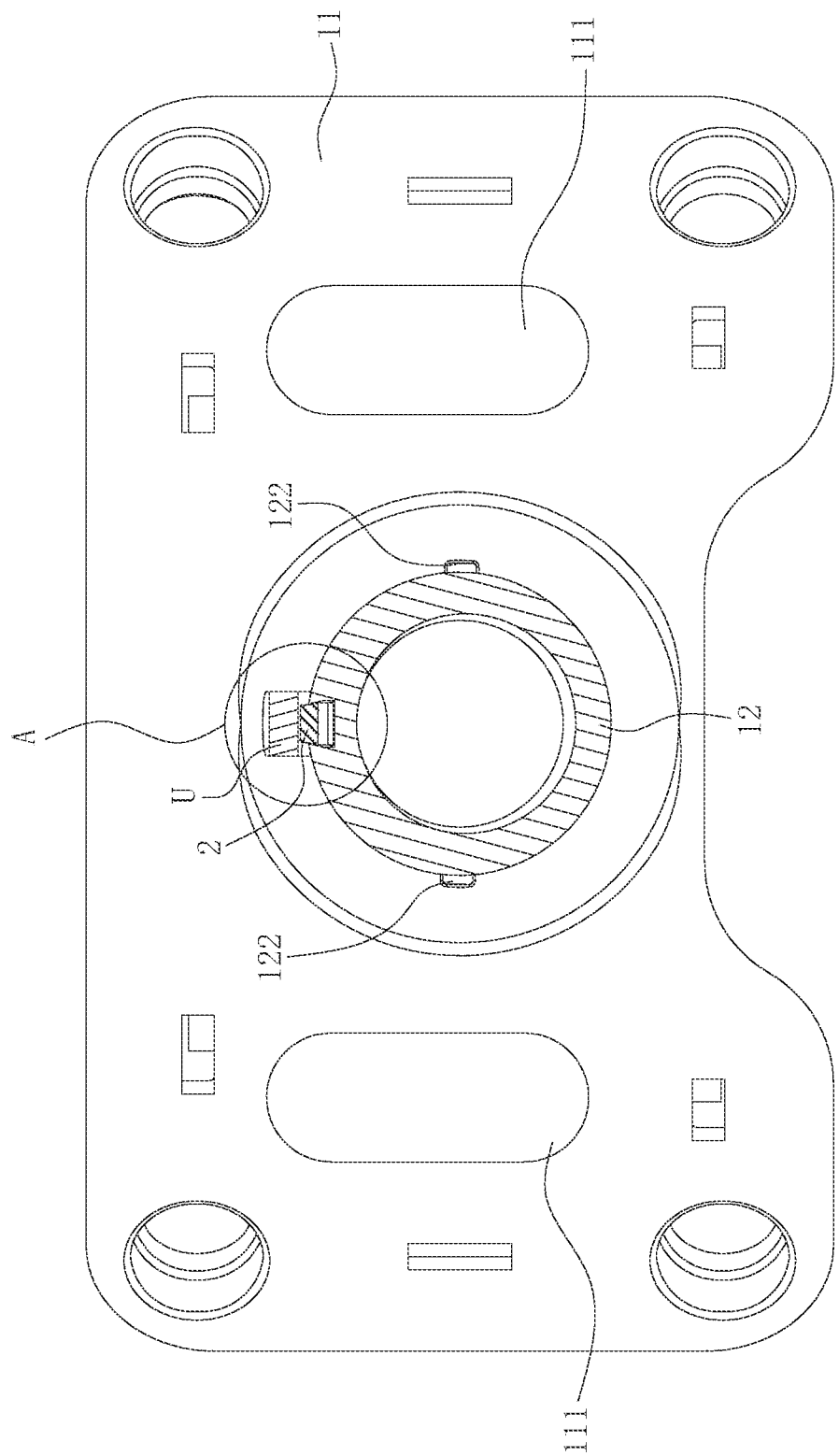
FIG. 10 is a cross-sectional view taken along a direction perpendicular to the front-rear direction when the locking element and the driving element are unlocked.
Figure 11:
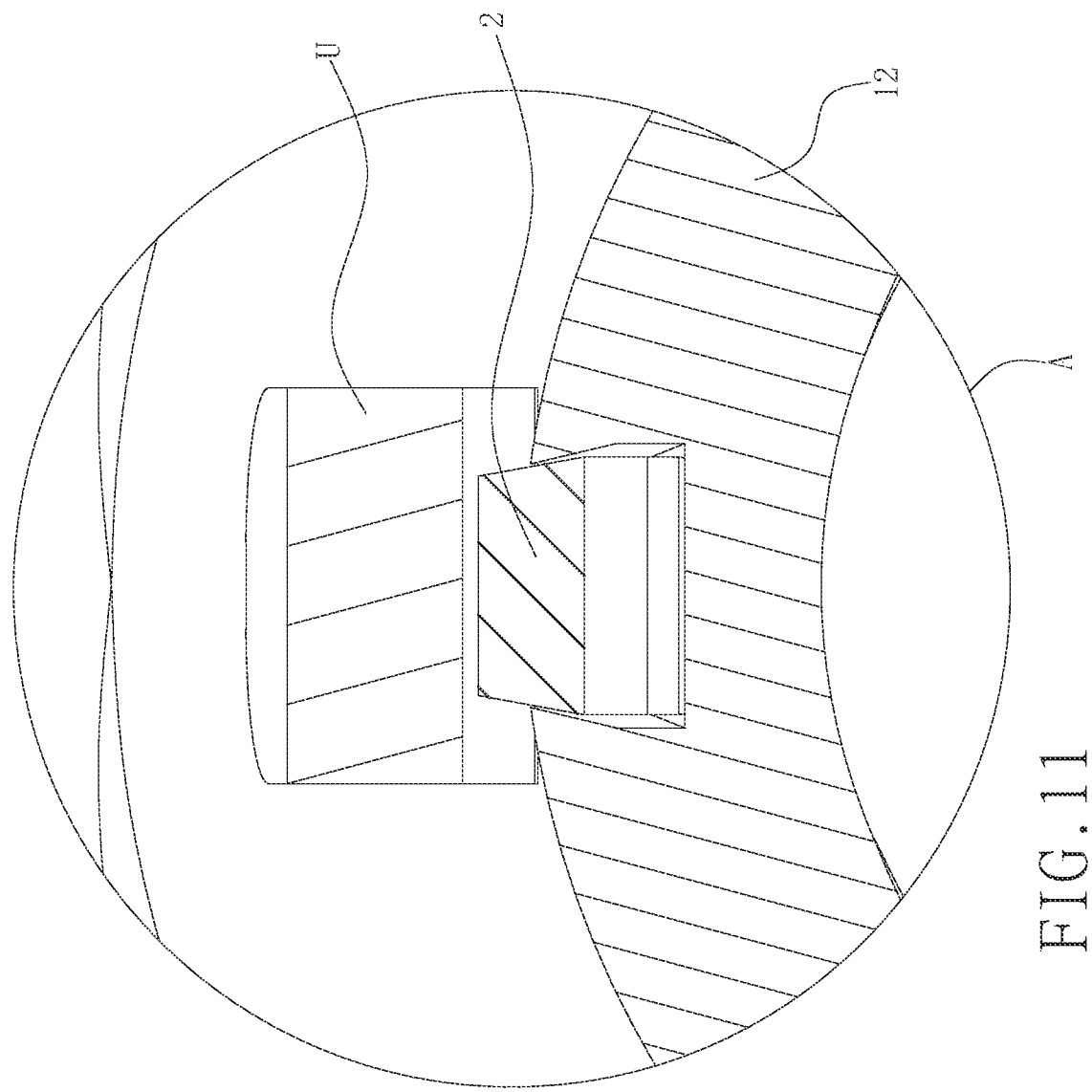
FIG. 11 is an enlarged view based on FIG. 10.

Referring to FIG. 10 and FIG. 11, there are shown cross-sectional views taken along the second direction at the limiting segment 1211 of the slot 121 when the locking element 2 is in an unlocked state. For description sake, the part of the locking element 2 proximate to the adjustment element 3 refers as a bottom, whereas the part distal to the adjustment element 3 refers as a top. The width of the top of the resilient arm 22 is less than the width of the top of the limiting segment 1211, whereas the width of the bottom of the resilient arm 22 is greater than the width of the top of the limiting segment 1211; hence, the resilient arm 22 cannot completely separate from the limiting segment 1211 of the slot 121 in the first direction, allowing the limiting segment 1211 to limit the position of the resilient arm 22 in the first direction, and allowing the least dimension of the limiting segment 1211 in the second direction to be less than the greatest dimension of the resilient arm 22 in the second direction, so as to limit the extent to which the resilient arm 22 bends and curves and thus mitigate the fatigue of the resilient arm 22 and extend the service life of the locking element 2.

Referring to FIG. 4 and FIG. 5, the adjustment element 3 is received in the passage portion 12 to assume a hollow-cored cylindrical shape. In this embodiment, the adjustment element 3 comprises a cylinder 31 and a rear lid 32. The outer surface of the cylinder 31 has outer thread which meshes with the inner thread of the passage portion 12. Owing to the outer and inner threads, the adjustment element 3 is rotatable and thus capable of undergoing forward and rearward displacement along the passage portion 12. Furthermore, owing to the outer and inner threads, the rear lid 32 is connected to the rear end of the cylinder 31. The outer surface of the cylinder 31 dents inward to form a positioning slot 311. The positioning slot 311 extends forward and rearward to receive the locking element 2 which has entered the passage portion 12. After the positioning slot 311 has received the locking element 2, the sidewall of the positioning slot 311 and the locking element 2 block each other, such that the adjustment element 3 is prevented from rotating along the threads and thus precluded from exiting and being admitted.

Figure 9:
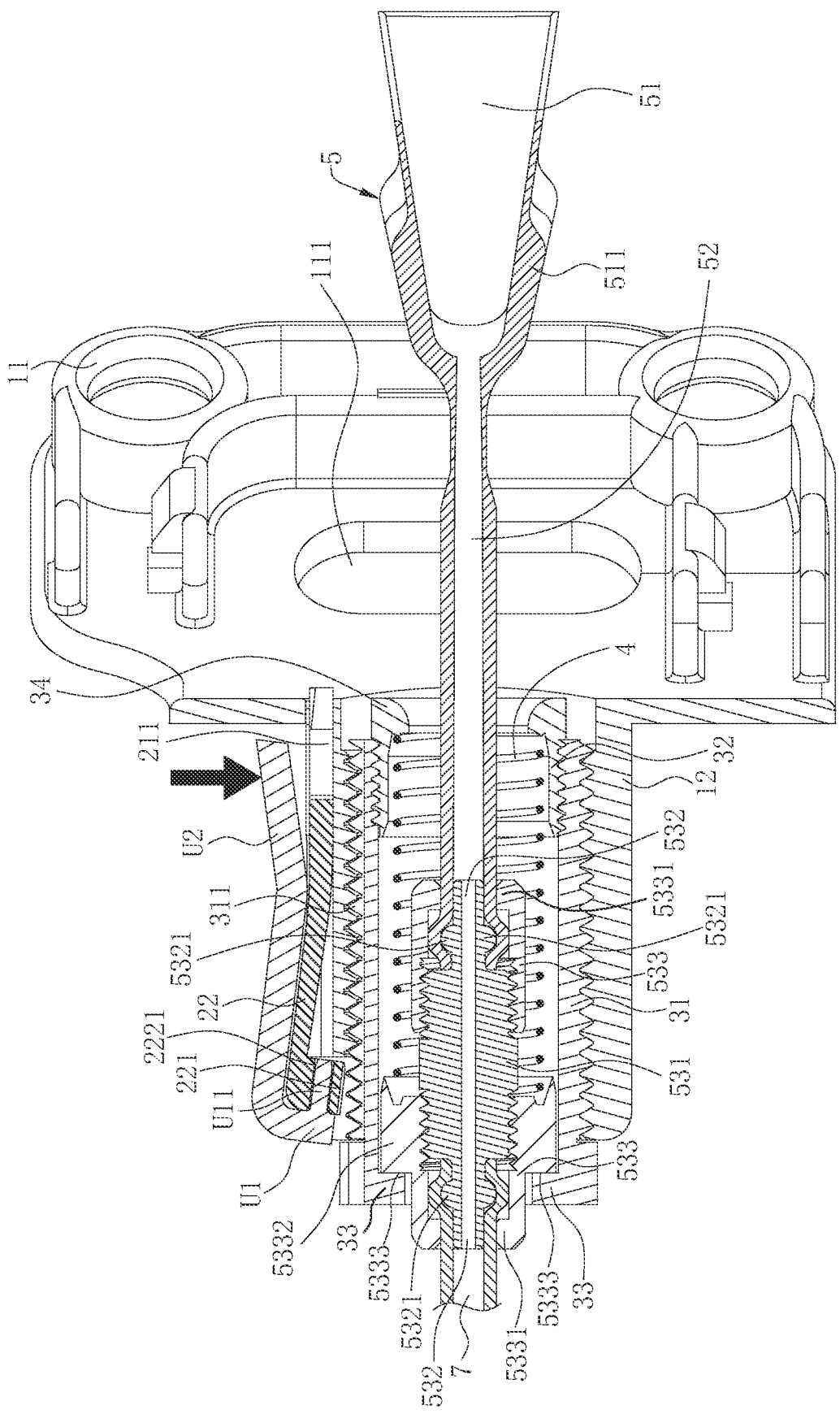
FIG. 9 is a schematic view based on FIG. 8, showing the driving element pressed and the locking element unlocked.

Referring to FIG. 8 and FIG. 9, the adjustment element 3 receives part of the resilient element 4 and part of the suction member 5. A front blocking member 33 is disposed at the front end of the inside of the cylinder 31 to limit the forward displacement of the suction member 5. A rear blocking member 34 is disposed in the rear lid 32 to prevent the resilient element 4 from protruding rearward beyond the adjustment element 3.

Referring to FIG. 8 and FIG. 9, the resilient element 4 connects the adjustment element 3 and the suction member 5, such that the suction member 5 and the adjustment element 3 move together forward and rearward. Owing to the user's tongue T, it is feasible for the suction member 5 to move forward and rearward relative to the adjustment element 3. The resilient element 4 provides a resilient force (required for position restoration) to the suction member 5 movable relative to the adjustment element 3, whereas the rear lid 32 and the cylinder 31 rotate relative to each other along the threads, such that the extent to which the resilient element 4 is compressed or extended can be adjusted, thereby adjusting the strength of the resilient force of the resilient element 4. In this embodiment, the resilient element 4 is a spring which fits around the suction member 5. The resilient element 4 has one end abutting against the suction member 5 and the other end abutting against the rear blocking member 34.

Referring to FIG. 2 and FIG. 8, the suction member 5 comprises a tongue fixing portion 51, a channel 52 connected to the tongue fixing portion 51, and a connector 53 connected to the channel 52. The tongue fixing portion 51 is pocket-shaped and encloses the front end of the user's tongue T. When the device is in operation, a negative pressure is transmitted to the tongue fixing portion 51, and an attractive force is formed between the inner surface of the tongue fixing portion 51 and the user's tongue T, such that the user's tongue T is fixed to the tongue fixing portion 51. The channel 52 extends into the adjustment element 3 to transmit the negative pressure to the tongue fixing portion 51. The connector 53 is held at the front end of the adjustment element 3 by the front blocking member 33 and the resilient element 4.

Figure 12:
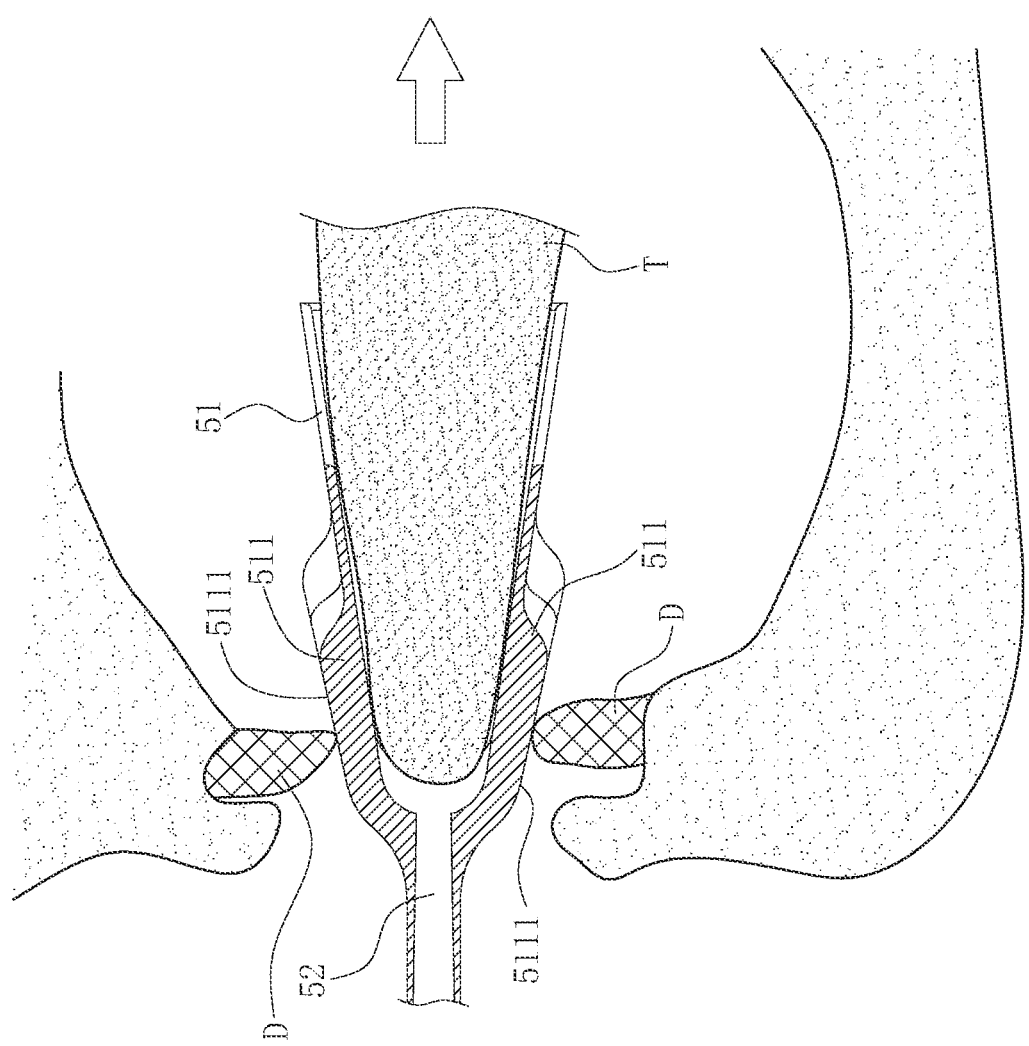
FIG. 12 is a schematic view of thickened portions disposed at a tongue fixing portion and abutting against an user's teeth.
Figure 13:
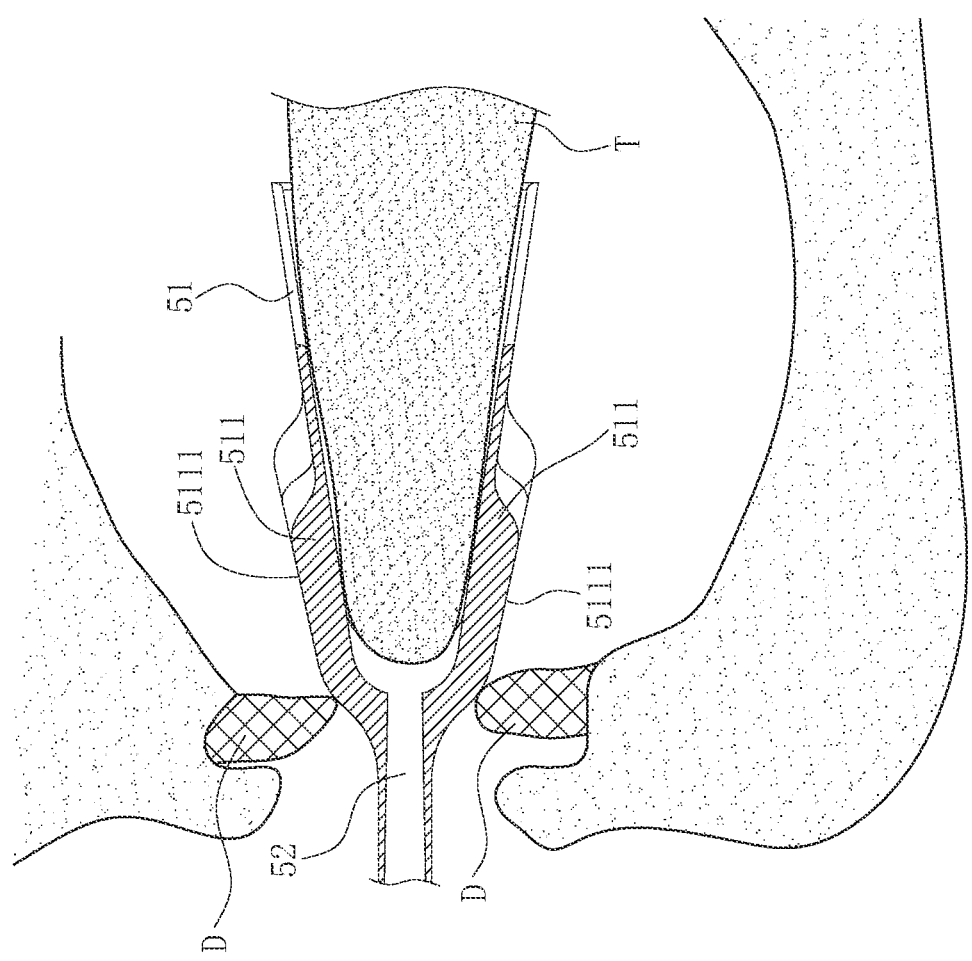
FIG. 13 is a schematic view based on FIG. 12, showing that the tongue fixing portion slides relative to the user's teeth.

Referring to FIG. 12 and FIG. 13, there are shown schematic views of how the user's tongue T is fixed in place under a negative pressure by the tongue fixing portion 51. The tongue fixing portion 51 is made of a soft material, such as silicone, and affixed to the surface of the user's tongue T to maintain the negative pressure. A thickened portion 511 is disposed on each of the upper and lower sides of the front end of the tongue fixing portion 51. The thickened portions 511 work between the user's upper and lower teeth D. The thickened portions 511 are thicker than the remaining part of the tongue fixing portion 51; hence, if the user's teeth D inadvertently abut against the thickened portions 511, an occlusion force transmitted to the user's tongue T will be mitigated and spread. The thickened portions 511 each have an oblique surface 5111 which is smooth and faces the user's teeth D. The two oblique surfaces 5111 on the upper and lower sides of the tongue fixing portion 51 approach each other gradually in the forward direction. When the upper and lower teeth D inadvertently abut against the oblique surfaces 5111, the tongue fixing portion 51 is compressed by the upper and lower teeth D and thus moved rearward, such that the user's teeth D slide forward across the oblique surfaces 5111 relative to the tongue fixing portion 51 until the tongue fixing portion 51 separates from the user's teeth D from behind.

Referring to FIG. 1, FIG. 8 and FIG. 9, the negative pressure source 6 is in communication with the connector 53 via a catheter 7, whereas the suction member 5 sucks on the user's tongue T under the negative pressure generated by the negative pressure source 6. The connector 53 is in communication with the channel 52 and the catheter 7. In this embodiment, the catheter 7 is U-shaped. Both the channel 52 and the catheter 7 are flexible hoses. The connector 53 comprises an axle portion 531 and two mouths 532 disposed at the front and rear ends of the axle portion 531, respectively. The mouth 532 at the front end is inserted into the catheter 7. The mouth 532 at the rear end is inserted into the channel 52. A convex portion 5321 protrudes radially from the outer surface of each mouth 532 and surrounds the mouth 532 to widen the catheter 7 fitting around one mouth 532 and widen the channel 52 fitting around the other mouth 532. The front and rear ends of the connector 53 each have a movable hermetic seal element 533. The hermetic seal element 533 is disposed at the rim of the mouth 532 and has a narrowed portion 5331 which protrudes radially and inward. The narrowed portion 5331 abuts against the corresponding channel 52 or the catheter 7, pressing the channel 52 or the catheter 7 tightly against the mouth 532. One of the widened catheter 7 and the widened channel 52 is clamped radially by the corresponding convex portions 5321 and the hermetic seal elements 533. In this embodiment, the hermetic seal elements 533 and the axle portion 531 are separately formed and connected by threads. In another embodiment, the hermetic seal elements 533 and the axle portion 531 are integrally formed, for example, the hermetic seal element 533 may be a snap, which can be opened by pressing.

Referring to FIG. 8 and FIG. 9, in this embodiment, the dimension of the hermetic seal elements 533 pressing against the channel 52 is less than the inner diameter of the resilient element 4 so as for the hermetic seal elements 533 to be received in the resilient element 4. The hermetic seal element 533 pressing against the catheter 7 has an enlarged portion 5332. The dimension of the enlarged portion 5332 is greater than the inner diameter of the resilient element 4, such that the enlarged portion 5332 abuts against one end of the resilient element 4 to bear the resilient force exerted by the resilient element 4, driving the suction member 5 to restore its initial position. The front end of the enlarged portion 5332 functions as a stopping portion 5333 which faces forward to abut against the front blocking member 33 and thereby limit the forward displacement of the tongue fixing portion 51 disposed at the rear end of the suction member 5.

Referring to FIG. 8 and FIG. 9, in this embodiment, the connector 53 and the channel 52 are separately formed. In another embodiment, the connector 53 and the channel 52 are integrally formed.

Figure 14:
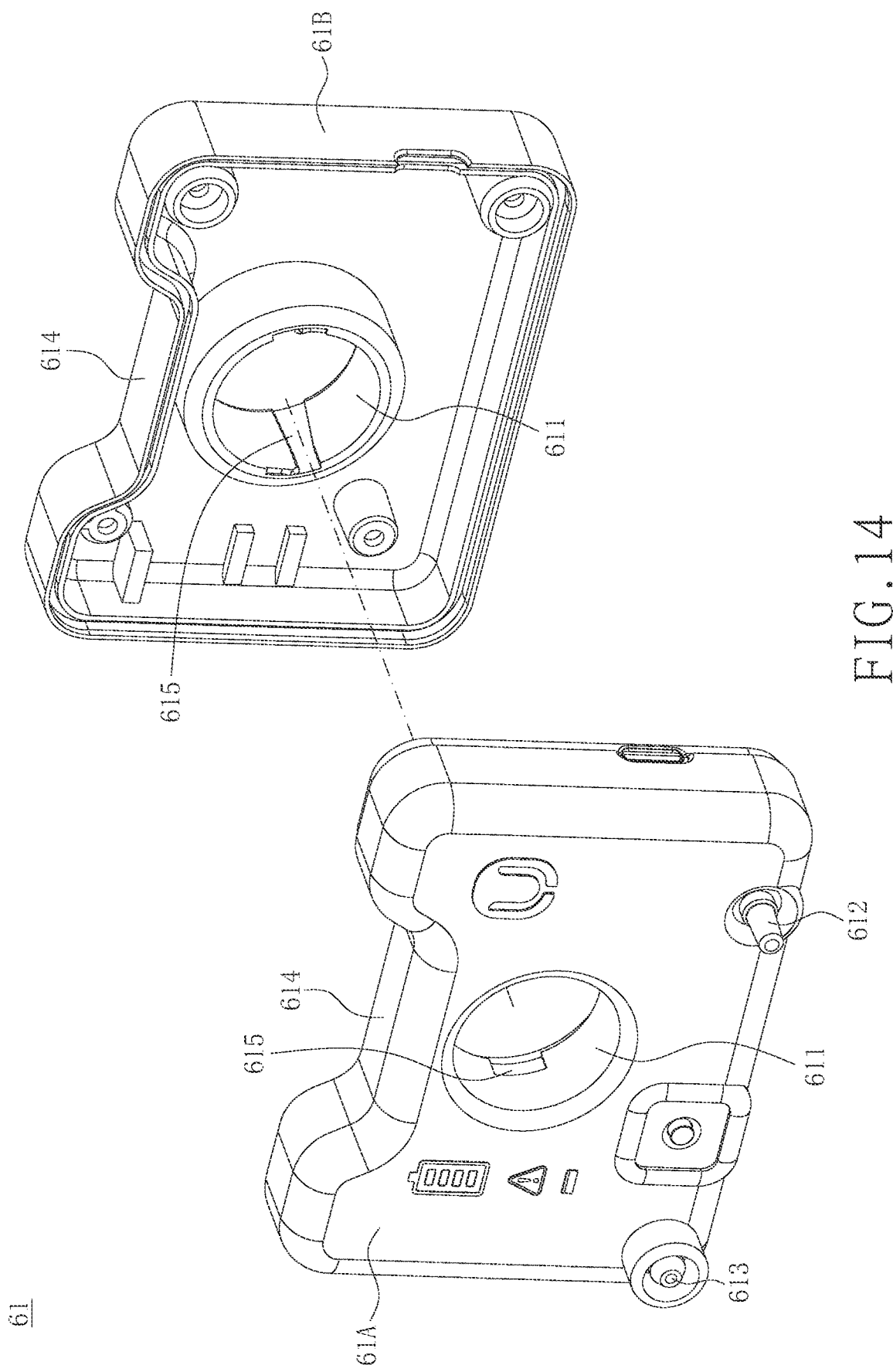
FIG. 14 is an exploded view of a casing of the negative pressure source of FIG. 1.
Figure 15:
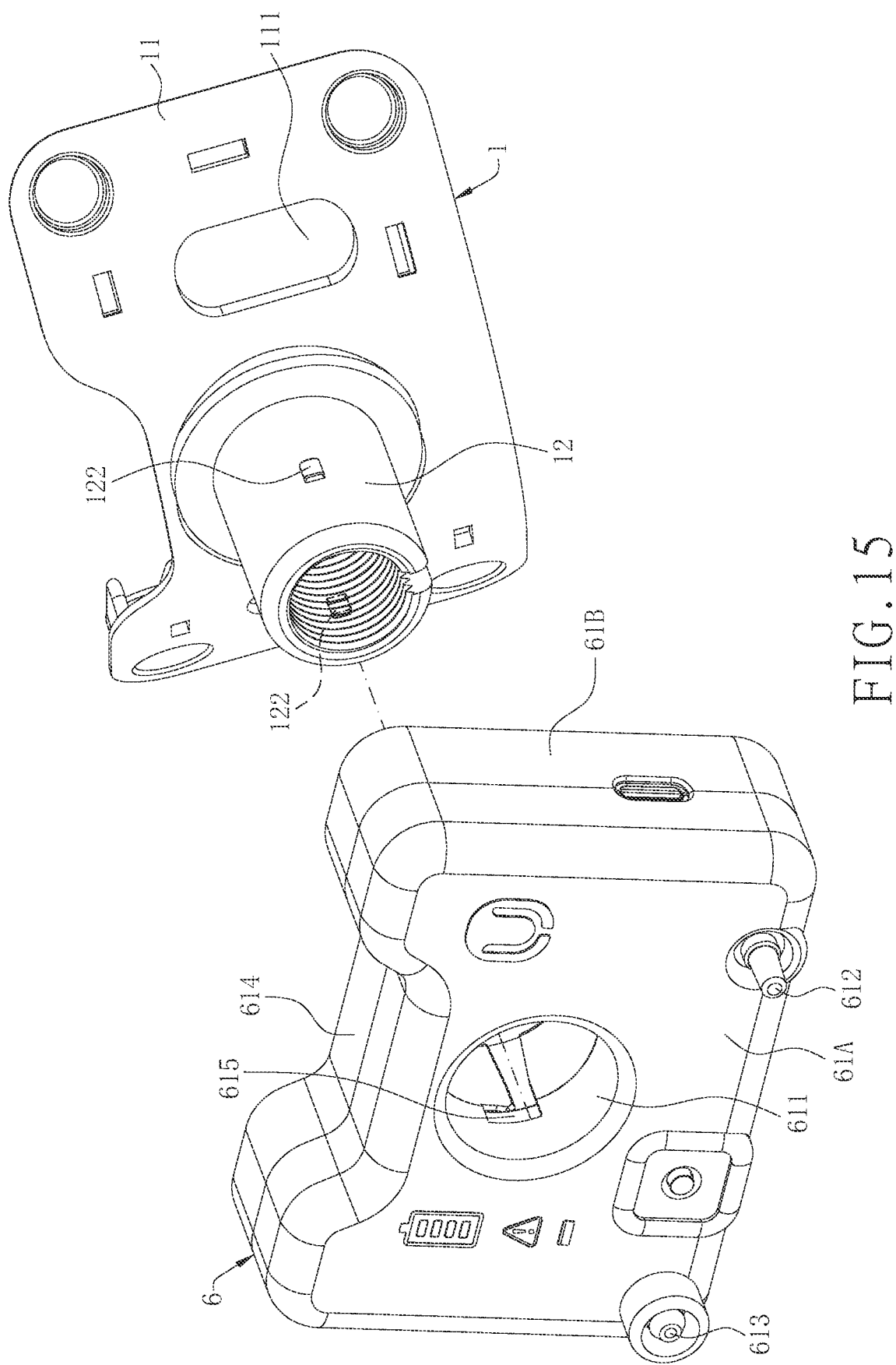
FIG. 15 is a schematic view of the negative pressure source and a base of FIG. 1, showing that the negative pressure source and the base are combined.

Referring to FIG. 1 and FIG. 14, the negative pressure source 6 is mounted on the base 1, such that the device for alleviating obstructive sleep apnea is a wearable device. The negative pressure source 6 is in communication with the channel 52 via the catheter 7 to provide a negative pressure to the tongue fixing portion 51. The negative pressure source 6 is an electrical module which comprises multiple functional components. The functional components are enclosed by an external casing 61. A through hole 611 is centrally disposed in the casing 61 and adapted to receive the passage portion 12. An inlet 612 is disposed on the front side of the casing 61 to admit the catheter 7 into the casing 61. An outlet 613 is disposed on the front side of the casing 61 to discharge gas. A accommodated depression 614 is disposed on the top side of the casing 61 to provide accommodated space to the user's nose.

Referring to FIG. 14 through FIG. 19, two rails 615 are concavely disposed on the surface of the through hole 611, and the two rails 615 are disposed on right and left sides of through hole 611. The casing 61 comprises a front case 61A and a rear case 61B. A seam 616 between the front case 61A and the rear case 61B passes through the rails 615. The rails 615 each comprise a guiding groove 6151 extending forward and rearward and crossing the seam 616 and a fixing recess 6152 connected to the guiding groove 6151. An included angle is formed between the direction in which the guiding groove 6151 extends and the direction in which the fixing recess 6152 extends. In this embodiment, the guiding groove 6151 extends in the axial direction (i.e., the front-rear direction) of the through hole 611. The fixing recess 6152 is perpendicular to the guiding groove 6151 and extends in the circumferential direction of the through hole 611. To combine the passage portion 12 and the casing 61, the operator moves the positioning protruding portion 122 along the guiding groove 6151 and then along the fixing recess 6152 before fixing the positioning protruding portion 122 to the fixing recess 6152. In another embodiment, the fixing recess 6152 extends on the inner surface of the through hole 611, and the included angle between the direction in which the guiding groove 6151 extends and the direction in which the fixing recess 6152 extends is not equal to 90 degrees.

Referring to FIG. 16 through FIG. 19, in this embodiment, part of the fixing recess 6152 extends rearward and crosses the seam 616 to form a fixing segment 6152A. The device further has an operating element 8. In this embodiment, the operating element 8 is a resilient rubber ring disposed between the rear case 61B and the mask portion 11. An assembly process entails exerting an external force on the negative pressure source 6 to enable the negative pressure source 6 to move toward the mask portion 11, such that the operating element 8 is compressed by the rear case 61B and the mask portion 11. After the positioning protruding portion 122 has entered the fixing recess 6152, the external force is no longer exerted on the negative pressure source 6 and the base 1, but the operating element 8 exerts resilient forces (acting in directions away from each other) on the rear case 61B and the mask portion 11, such that the positioning protruding portion 122 and the fixing recess 6152 move relative to each other in the front-rear direction until the positioning protruding portion 122 enters the fixing segment 6152A. The rails 615 each further comprise an engaging member 6153. The engaging member 6153 is disposed between the fixing segment 6152A and the guiding groove 6151. The operating element 8 keeps exerting a force in the front-rear direction, and the engaging member 6153 blocks the positioning protruding portion 122 in the circumferential direction of the through hole 611; hence, the positioning protruding portion 122 is unable to reverse and retreat from the fixing recess 6152, thereby fixing the negative pressure source 6 and the base 1 to each other.

Figure 16:
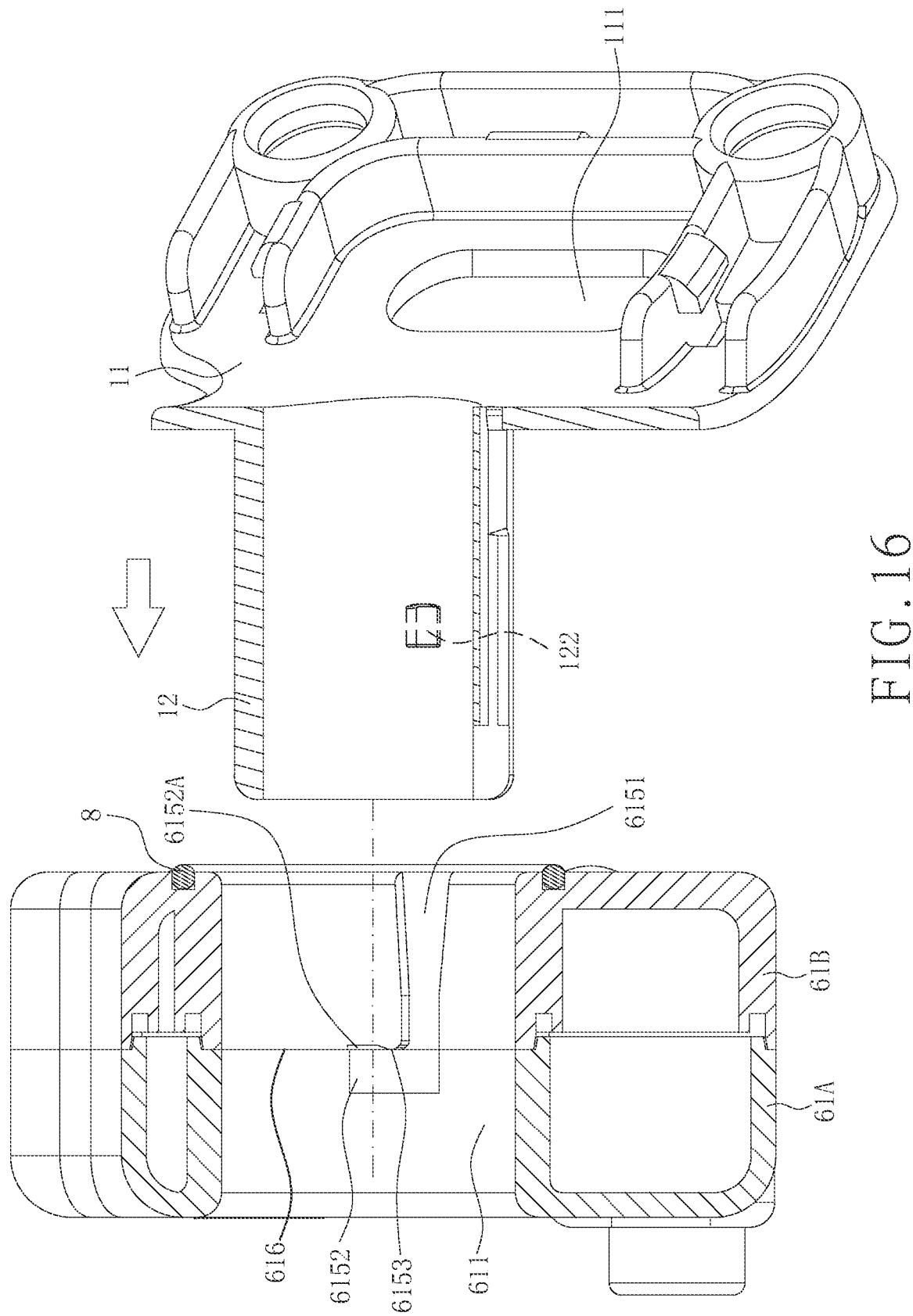
FIG. 16 is a cross-sectional view taken along the front-rear direction of FIG. 15.
Figure 17:
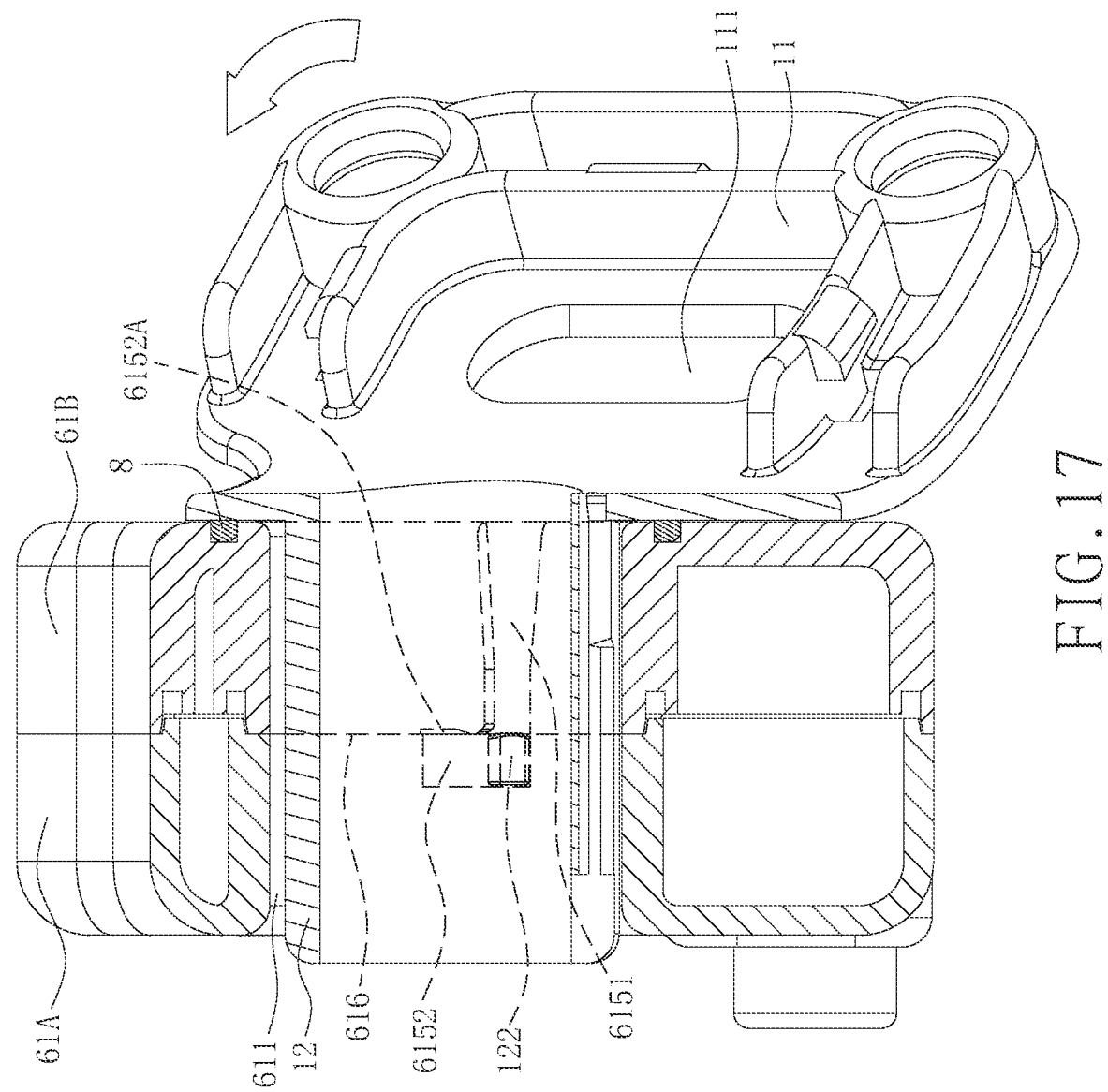
FIG. 17 is a schematic view based on FIG. 16, showing that a positioning protruding portion has entered a guiding groove of a rail.
Figure 18:
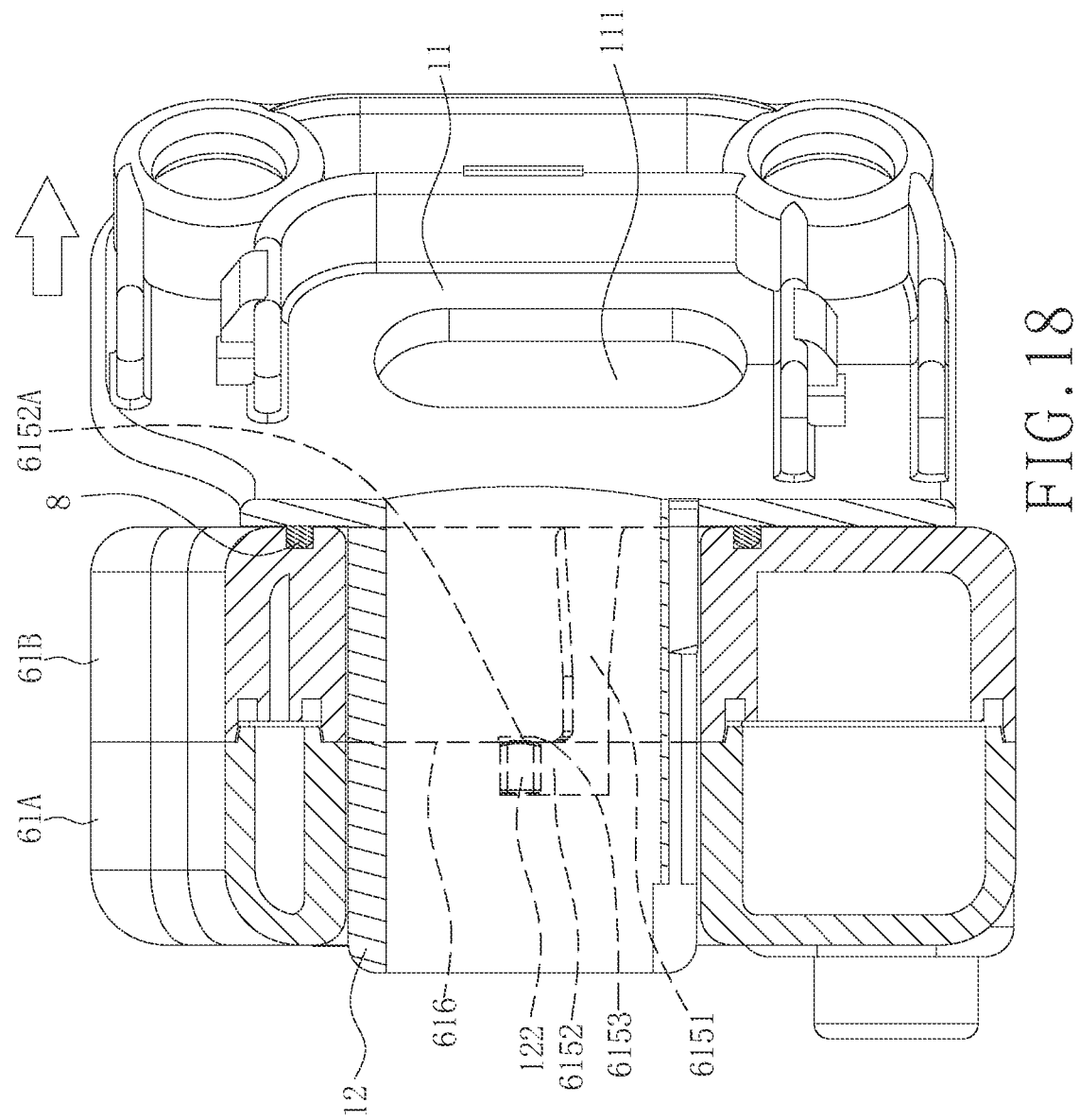
FIG. 18 is a schematic view based on FIG. 17, showing that the positioning protruding portion has entered a fixing recess of the rail, with its operating element compressed and restrained.
Figure 19:
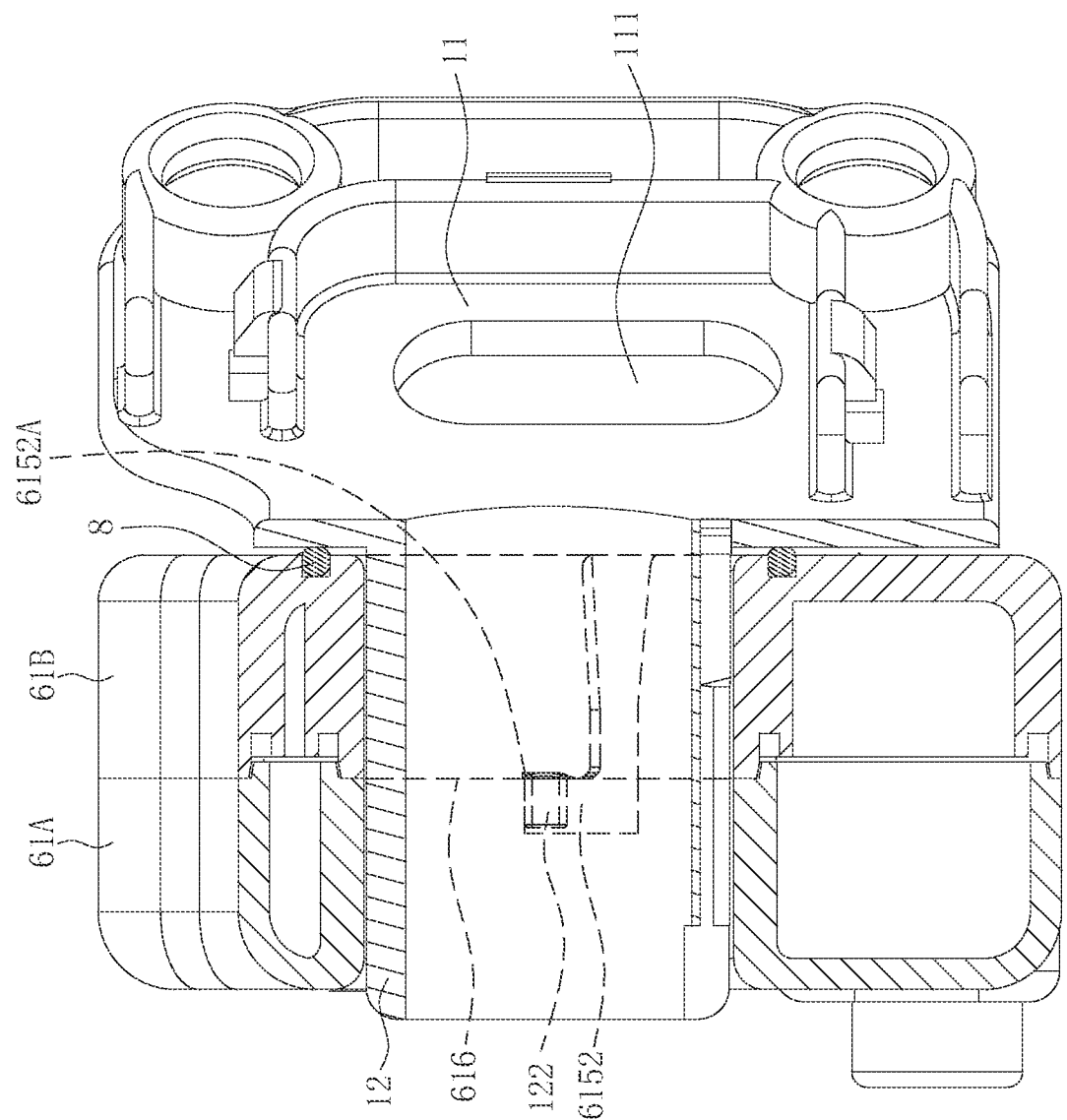
FIG. 19 is a schematic view based on FIG. 18, showing that the positioning protruding portion has entered a fixing segment, with its operating element released.

Referring to FIG. 14 and FIG. 16, in this embodiment, the fixing segment 6152A extends away from the guiding groove 6151 and crosses the seam 616. In other words, the fixing recess 6152 is formed by fitting the front case 61A and the rear case 61B together. Both the fixing segment 6152A and the engaging member 6153 are disposed on the rear case 61B, whereas the remaining part of the fixing recess 6152 is disposed on the front case 61A, so as to simplify the injection molding process required for forming the fixing recess 6152.

In another embodiment, the fixing segment 6152A extends in the same direction as the guiding groove 6151 and crosses the seam 616. Both the fixing segment 6152A and the engaging member 6153 are disposed in the front case 61A, whereas the remaining part of the fixing recess 6152 is disposed in the rear case 61B. The positioning protruding portion 122 enters the fixing segment 6152A and blocks the engaging member 6153, so as to prevent the detachment of the positioning protruding portion 122. The operating element 8 exerts a force under which the rear case 61B and the mask portion 11 approach each other. The operating element 8 is, for example, a clamp. In another embodiment, the rails 615 are disposed on the outer surface of the passage portion 12, and the positioning protruding portion 122 is disposed on the inner surface of the through hole 611.

In this embodiment, the casing 61 and the base 1 are separately manufactured and thereafter separably fitted together. In another embodiment, parts of the casing 61, namely the front case 61A and/or the rear case 61B, can be integrally formed with the base 1.

Figure 20:
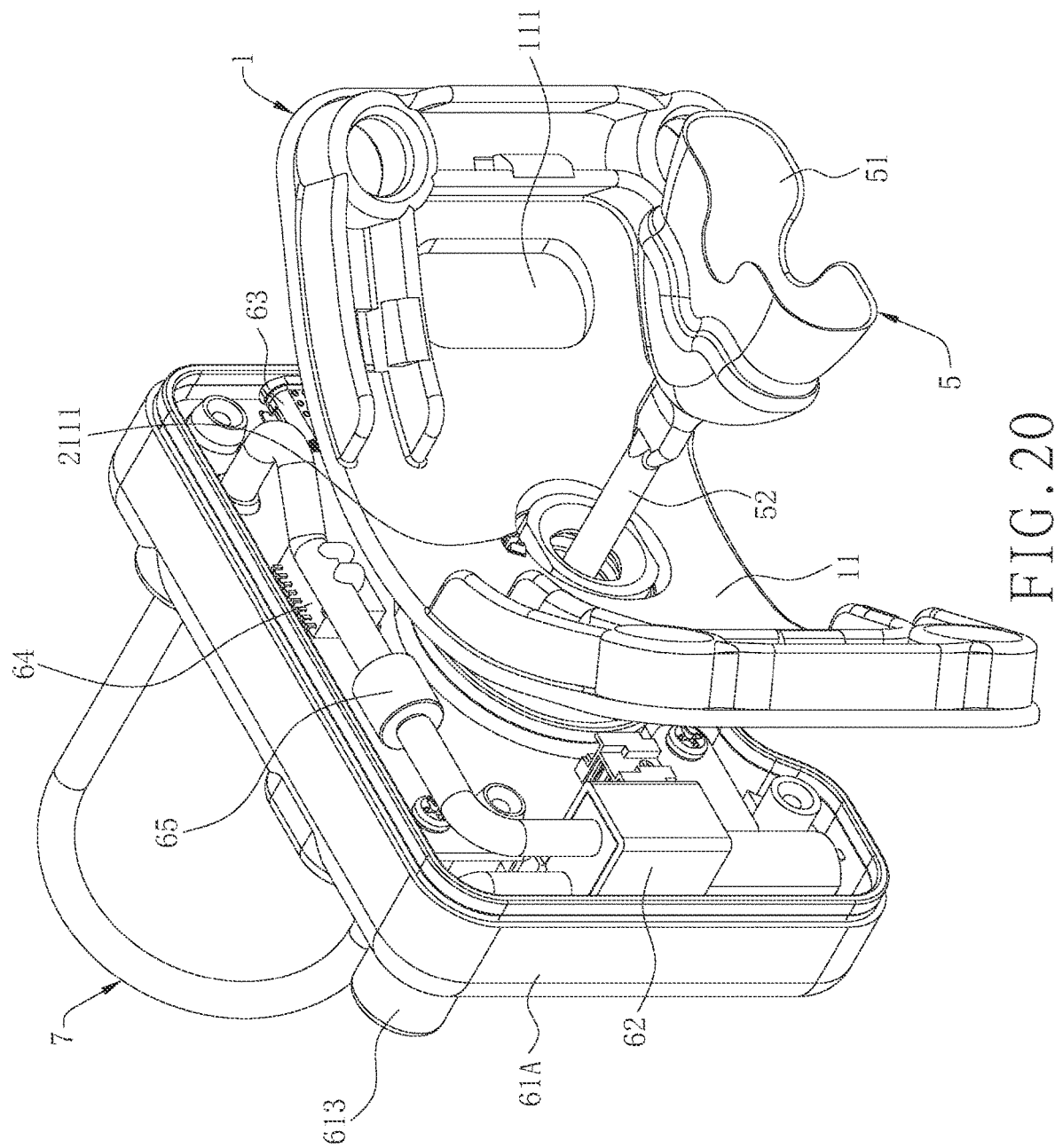
FIG. 20 is a schematic view of the components of the negative pressure source.
Figure 21:
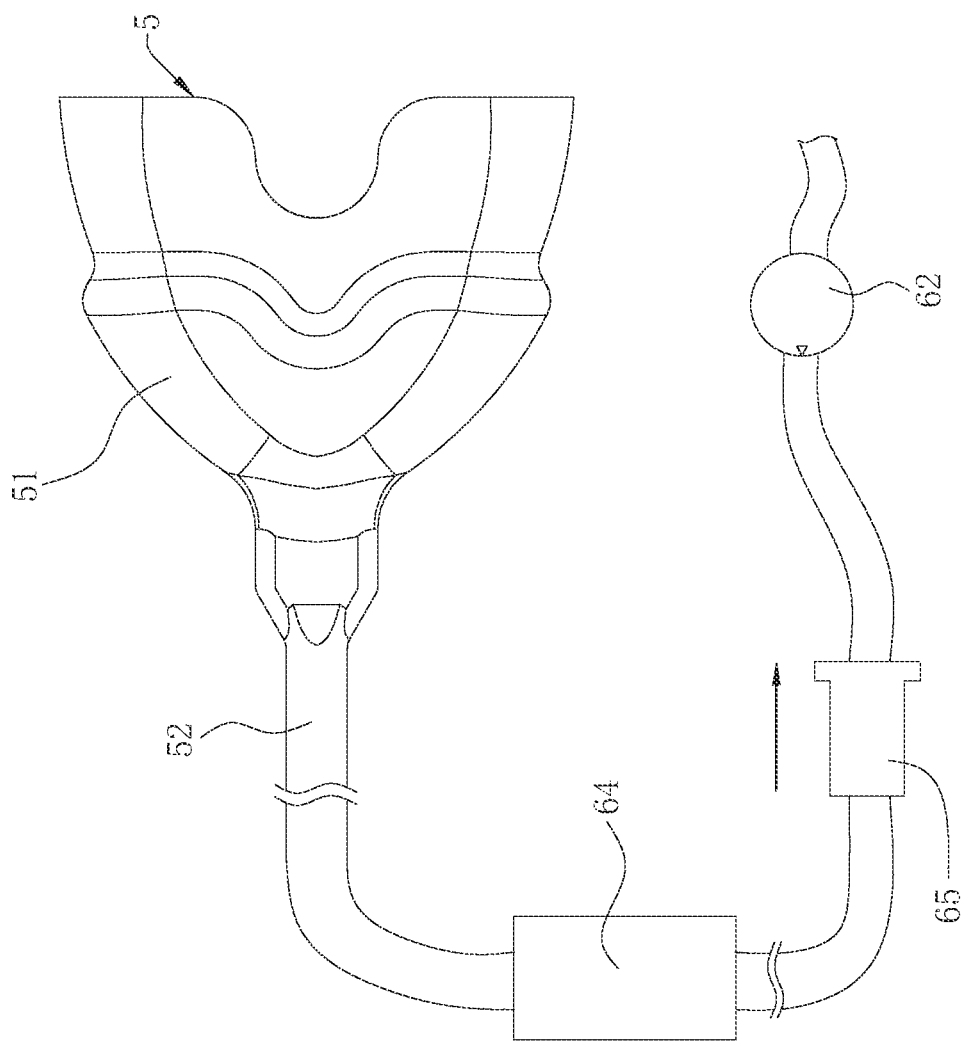
FIG. 21 is a schematic view of the tongue fixing portion, negative pressure sensor, check valve and negative pressure pump in communication with each other.
Figure 22:
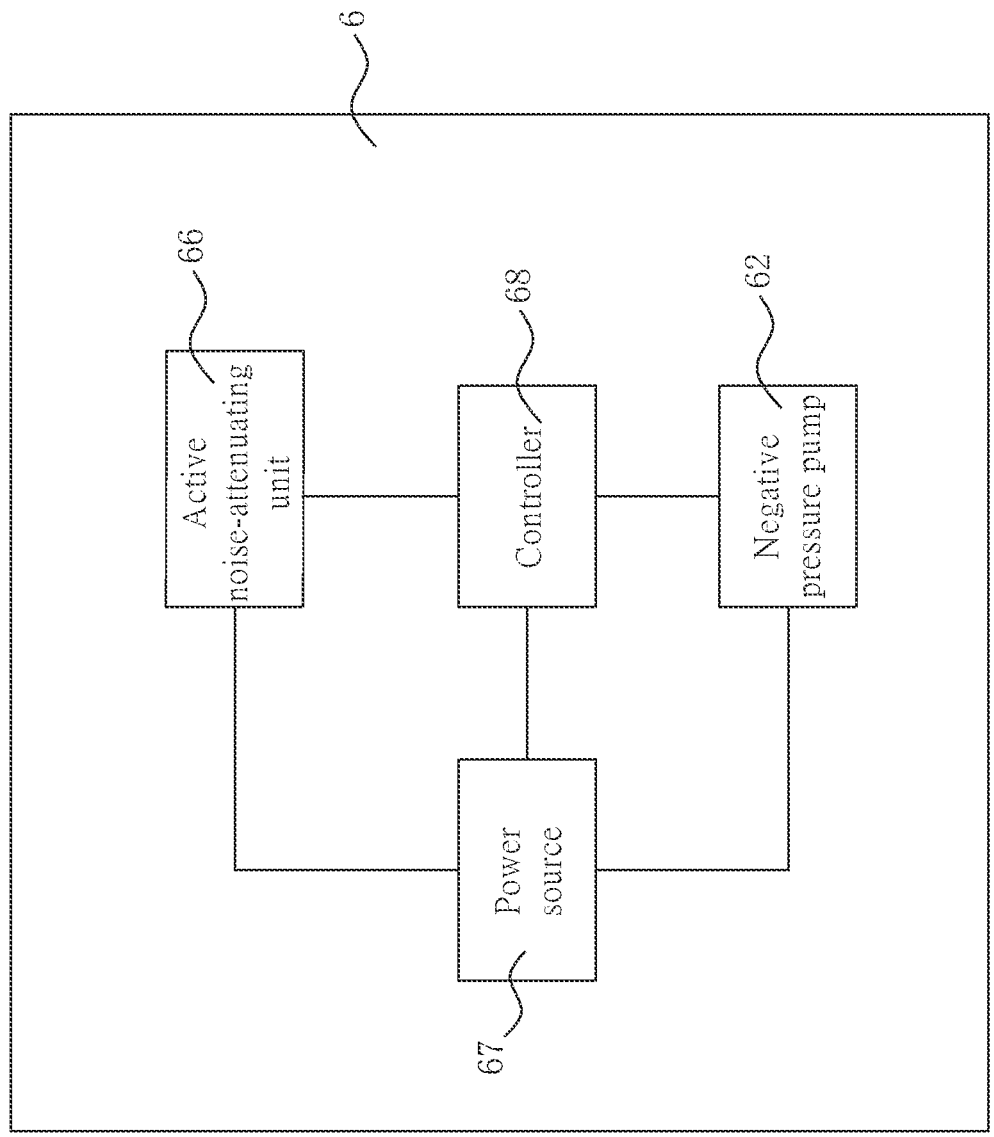
FIG. 22 is a schematic view of an active noise-attenuating unit, controller, negative pressure pump and power source connected to each other.

Referring to FIG. 20, FIG. 21 and FIG. 22, the negative pressure source 6 essentially comprises a negative pressure pump 62, a power source 67 for supplying power to the negative pressure pump 62 and the like, an electrical connector 63 for use in external connection, a negative pressure sensor 64, a check valve 65 disposed between the negative pressure pump 62 and the negative pressure sensor 64, and a controller 68 for receiving and sending a control signal. The negative pressure pump 62 can be a conventional, small-sized air extracting pump. As suggested by conventional wisdom, the negative pressure pump 62 in operation extracts gas in order to generate a negative pressure, and the target area for air extraction is located at the tongue fixing portion 51. The extracted gas is delivered to the inside of the negative pressure source 6 via the channel 52, the connector 53, and the catheter 7 sequentially. Inside the negative pressure source 6, the extracted gas is sensed with the negative pressure sensor 64. The negative pressure sensor 64 is a conventional digital barometric pressure sensor. The negative pressure sensor 64 is in communication with the tongue fixing portion 51 and thereby can monitor the magnitude of the negative pressure at the tongue fixing portion 51. Then, a measurement obtained by the negative pressure sensor 64 is sent to the controller 68. If the measurement is less than a threshold, the controller 68 will increase the operating power of the negative pressure pump 62; otherwise, the controller 68 will decrease the operating power of the negative pressure pump 62. After being sensed with the negative pressure sensor 64, the extracted gas passes through the check valve 65. The check valve 65 is a conventional non-return ball valve dedicated to medical uses. The check valve 65 only permits the gas to flow unidirectionally from the tongue fixing portion 51 to the negative pressure pump 62. Finally, the negative pressure pump 62 enables the extracted gas to be discharged from the negative pressure source 6 via the outlet 613.

In an ideal situation, even if the negative pressure pump 62 stops operating, a hermetically-sealed space required to maintain the negative pressure can be formed between the user's tongue T and the check valve 65. Thus, the controller 68 causes the negative pressure pump 62 to stop operating and thus reduces power consumption as soon as the negative pressure sensor 64 detects that the negative pressure between the user's tongue T and the check valve 65 is sufficient to keep the user's tongue T and the tongue fixing portion 51 fixed to each other. In case of an insufficient negative pressure between the user's tongue T and the check valve 65 because of the muscular activity of the user's tongue T or for any other reasons, the controller 68 will restart the negative pressure pump 62 according to related measurements obtained by the negative pressure sensor 64.

Referring to FIG. 20 and FIG. 21, in this embodiment, before the extracted gas passes through the check valve 65, the negative pressure sensor 64 directly senses and measures the magnitude of the negative pressure at the tongue fixing portion 51. Further, the check valve 65 shuts out the effect of the negative pressure pump 62 on the negative pressure sensor 64.

In this embodiment, the power source 67 is a built-in rechargeable battery, such as a lithium battery, disposed in the casing 61 and connected to the electrical connector 63 while being recharged. In order to reduce risks associated with the recharging process, the controller 68 instructs the negative pressure pump 62 to stop operating according to a signal which indicates that the power source 67 is being recharged during the recharging process carried out to the power source 67. In other words, the device is not available for use to prevent users from using the device whenever the recharging process carried out to the power source 67 is underway.

Referring to FIG. 22, in this embodiment, an active noise-attenuating unit 66 is disposed, in an integrated manner, in the negative pressure source 6. As shown in the diagram, the negative pressure source 6 is depicted by a square, because the constituent elements of the active noise-attenuating unit 66 are separately distributed inside the negative pressure source 6. The diagram also shows the connective relationship between the negative pressure pump 62 and the controller 68. The active noise-attenuating unit 66 receives power from the power source 67 and electrically connects to the controller 68 in order to send signals. The active noise-attenuating unit 66 attenuates noise generated as a result of the operation of the negative pressure pump 62. The active noise-attenuating unit 66 comprises microphones for receiving sound waves of the noise, a noise-attenuating circuit, and speakers for generating reversed phase sound waves. The microphones, circuit and speakers are not shown in the diagram. The microphones are disposed in the vicinity of the negative pressure pump 62 to receive the noise sound waves from different angles. The microphones convert the received noise sound waves into corresponding noise signals. The noise-attenuating circuit comprises sub-circuits, such as an operator, register, rectifier, and amplifier. The operator generates actual reversed phase sound wave signals according to the received noise signals. The register has a built-in noise signal model for use by the negative pressure pump 62. Before the operator receives the noise signals generated by the microphones, the register sends the built-in noise signal model to the operator, such that the operator generates predetermined reversed phase sound wave signals before generating actual opposite-phase sound wave signals. The speakers are disposed in the vicinity of the negative pressure pump 62 to send reversed phase sound waves at different angles. In response to the received reversed phase sound wave signals, actual or predetermined, the speakers generate reversed phase sound waves for offsetting the noises of the negative pressure source 6.

Since the generation of the predetermined reversed phase sound wave signals precedes the generation of the actual reversed phase sound wave signals, the predetermined reversed phase sound waves (i.e., first noise-attenuated sound waves) precede the actual reversed phase sound waves (i.e., second noise-attenuated sound waves). Furthermore, since the first noise-attenuated sound waves are not strictly out of phase with the actual noises, their superposition fails to completely offset the noises of the negative pressure source 6 but ends up with residual noise sound waves. The residual noise sound waves undergo superposition with actual noise sound waves and are received by the microphones to undergo the next instance of active noise-attenuation, so as to generate the second noise-attenuated sound waves.

In this embodiment, the power supply to both the negative pressure pump 62 and the active noise-attenuating unit 66 is carried out by the power source 67 and controlled simultaneously by the controller 68. The active noise-attenuating unit 66 and the negative pressure pump 62 are started simultaneously and shut down simultaneously according to a control signal from the controller 68. Thus, it is only when the negative pressure pump 62 operates that the active noise-attenuating unit 66 is powered to function, so as to reduce power consumption of the active noise-attenuating unit 66 and extend endurance of the power source 67.

Figure 23:
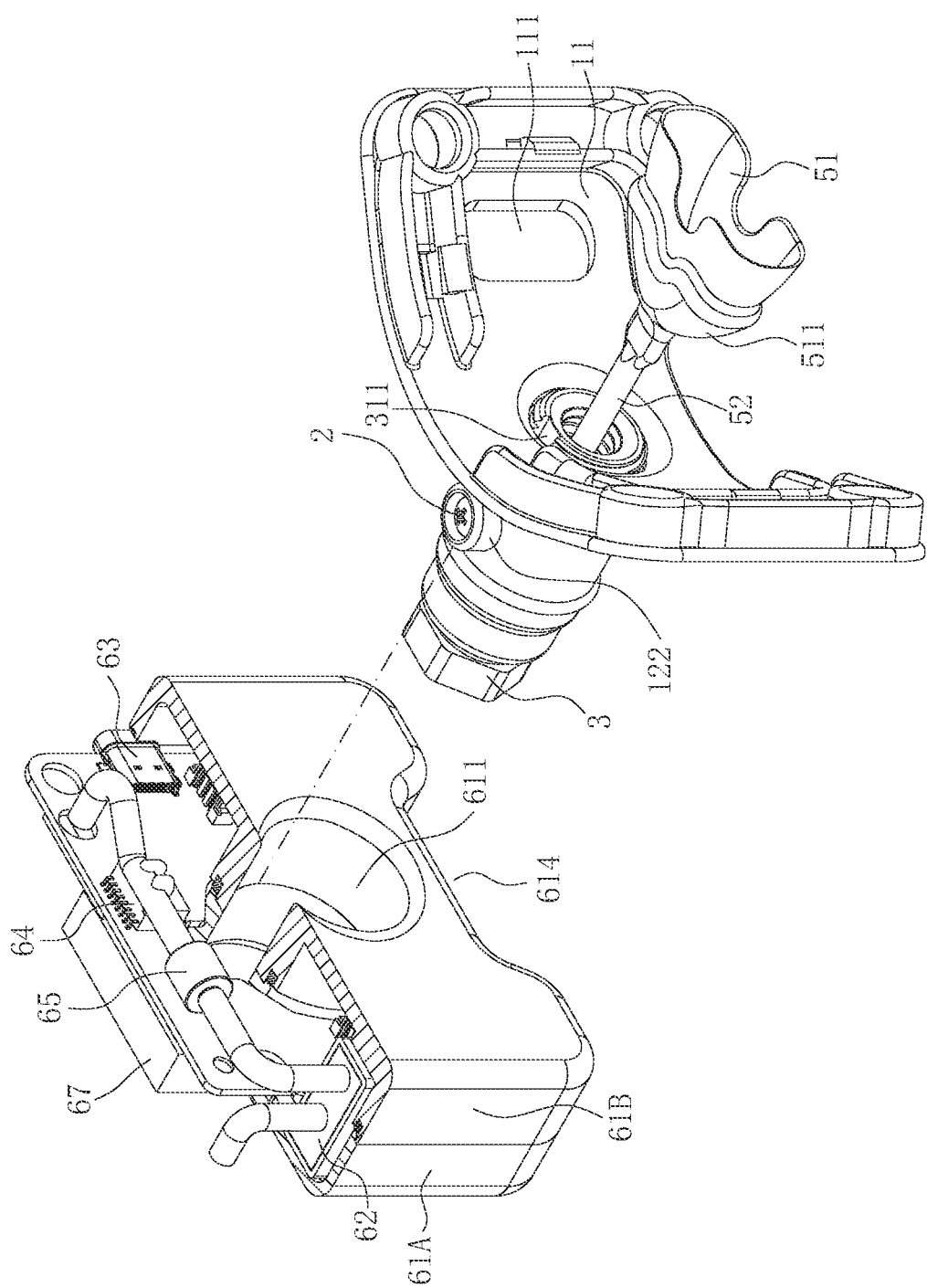
FIG. 23 is an exploded view of a device for alleviating obstructive sleep apnea according to the second embodiment of the present disclosure.
Figure 24:
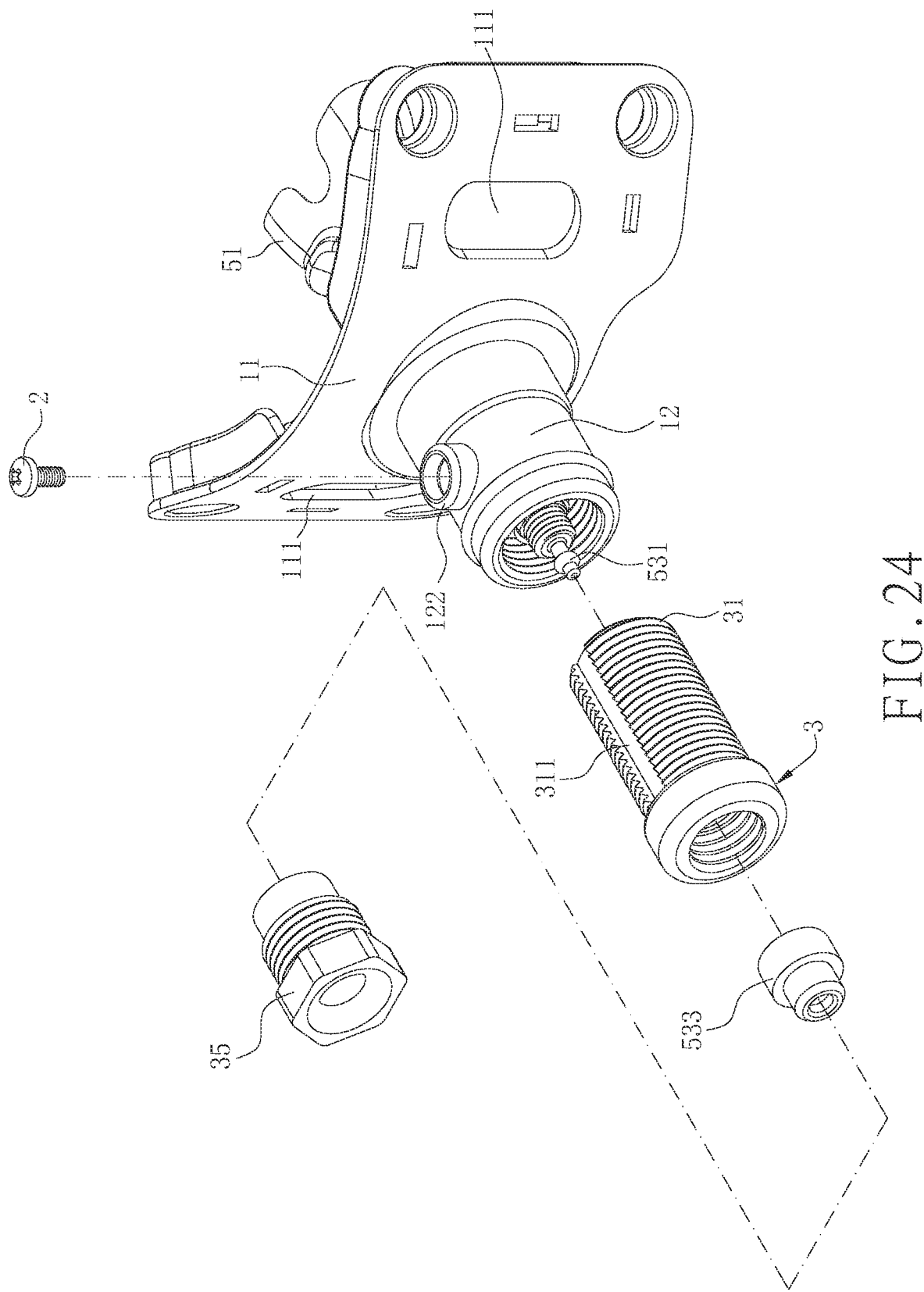
FIG. 24 is an exploded view based on FIG. 23, showing a base, a locking element, a suction member and an adjustment element.
Figure 25:
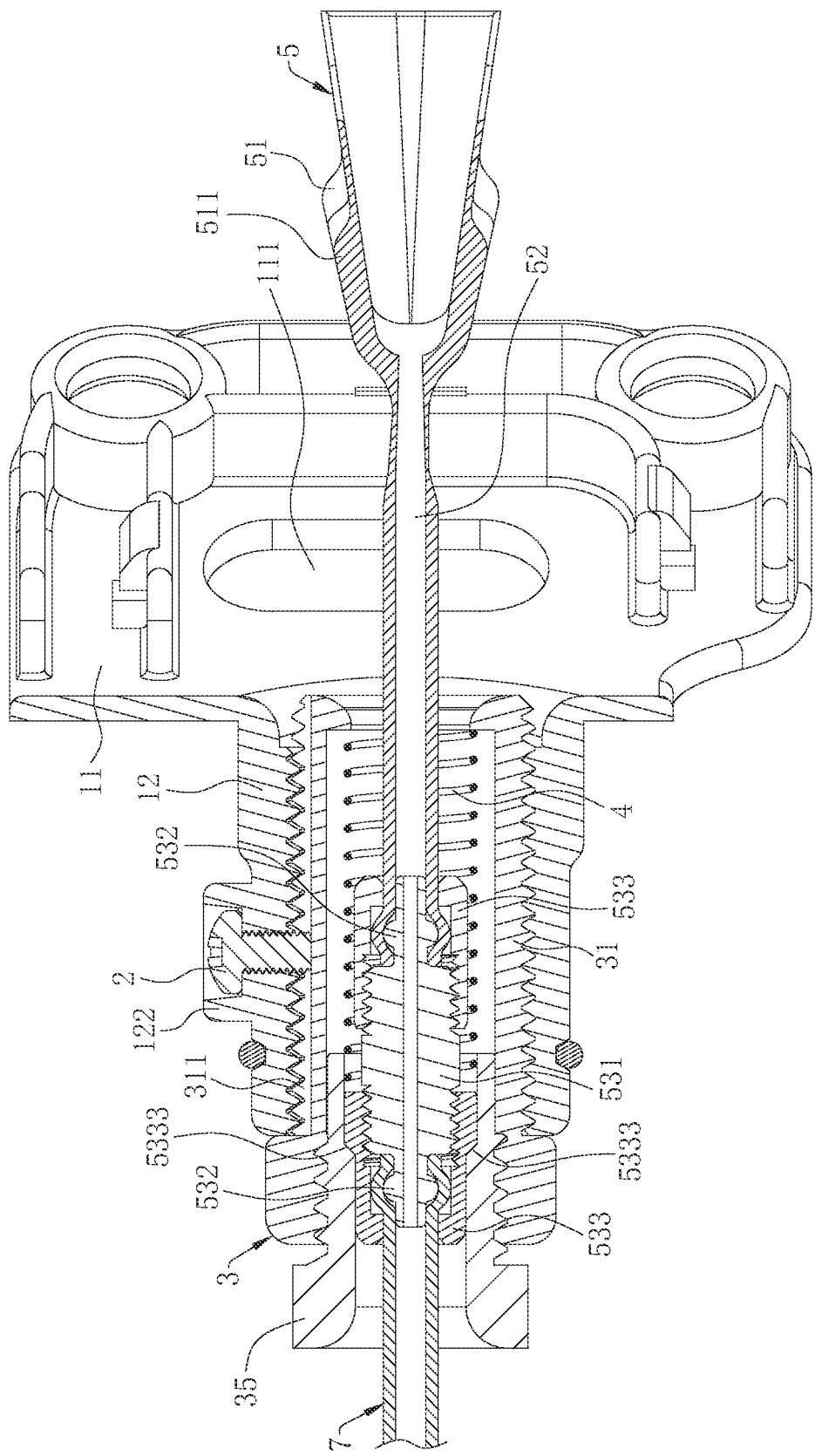
FIG. 25 is a cross-sectional view taken along the front-rear direction of FIG. 24 after assembly.

Referring to FIG. 23 through FIG. 25, a device for alleviating obstructive sleep apnea is provided according to the second embodiment of the present disclosure. In this embodiment, the locking element 2 is a screw. The outer surface of the passage portion 12 only has one positioning protruding portion 122 which radially protrudes. The positioning protruding portion 122 has a threaded hole which is in communication with the inside and outside of the passage portion 12. The locking element 2 meshes with the threaded hole. The bottom of the screw of the locking element 2 functions as the locking portion 221 and enters the positioning slot 311 to fix the adjustment element 3 in place. In this embodiment, the locking element 2 is unlocked and locked with a common, appropriate screwdriver.

Referring to FIG. 23, the negative pressure pump 62, the negative pressure sensor 64, the check valve 65 and the power source 67 are received in the casing 61.

Referring to FIG. 24 and FIG. 25, unlike the first embodiment, the second embodiment has the following distinguishing technical features. The adjustment element 3 does not have the rear lid. The adjustment element 3 comprises a front lid 35 disposed at the front end of the cylinder 31. The front blocking member 33 is disposed on the front lid 35 to prevent the escape of the suction member 5 from the front opening of the adjustment element 3. The rear blocking member 34 is disposed at the rear end of the cylinder 31. In this embodiment, the front lid 35 is received at the front end of the adjustment element 3 by thread-based meshing. In another embodiment, the front lid 35 is connected to the inside or outside of the adjustment element 3 by any other means.

According to the present disclosure, the device for alleviating obstructive sleep apnea has advantages as follows:

(1) A user plays an active role in operating the adjustment element 3, such that the suction member 5 undergoes relative displacement relative to the passage portion 12 together with the adjustment element 3 to thereby alter the course of pulling the user's tongue T, thereby minimizing the user's discomfort while the user is receiving therapy for obstructive sleep apnea.

(2) The negative pressure source 6 is mounted on the base 1, such that the device, including the negative pressure source 6, can be worn on the user's head to thereby not only shorten the required length of the catheter 7 connecting the patient and the negative pressure source 6 but also prevent the catheter 7 from being pressed, entangled or stretched. Furthermore, with the catheter 7 being short, the resistance to the flow of the gas flowing through the catheter 7 decreases, such that the required operating power of the negative pressure source 6 and thus the noise and weight of the negative pressure source 6 can be minimized.

(3) Since the course of the movement of the adjustment element 3 is fixed with the locking element 2, the adjustment element 3 can be reused conveniently, so as to avoid the hassle of providing the adjustment element 3 repeatedly.

(4) Before the extracted gas passes through the check valve 65, the negative pressure sensor 64 directly senses and measures the magnitude of the negative pressure at the tongue fixing portion 51. Further, the check valve 65 shuts out the effect of the negative pressure pump 62 on the negative pressure sensor 64.

(5) The active noise-attenuating unit 66 has a built-in noise signal model for use by the negative pressure pump 62. Before receiving noise signals generated by the microphones, the register sends the built-in noise signal model to the operator. Thus, the operator generates predetermined reserved phase sound wave signals before generating actual reversed phase sound wave signals, so as to achieve preliminary noise attenuation and enhance user experience.

(6) The power supply to both the negative pressure pump 62 and the active noise-attenuating unit 66 is carried out by the power source 67 and controlled simultaneously by the controller 68. The active noise-attenuating unit 66 and the negative pressure pump 62 are started simultaneously and shut down simultaneously by the controller 68 according to measurements obtained by the negative pressure sensor 64. Thus, it is only when the negative pressure pump 62 operates that the active noise-attenuating unit 66 is powered to function, so as to reduce power consumption of the active noise-attenuating unit 66 and extend endurance of the power source 67.

(7) The adjustment element 3 comprises the cylinder 31 and the rear lid 32 or comprises the cylinder 31 and the front lid 35. The rear lid 32 and the front lid 35 connect to the cylinder 31 by thread-based meshing and move forward and rearward relative to the cylinder 31; hence, the resilient element 4 has one end abutting against the cylinder 31 and the other end abutting against the rear lid 32 or the front lid 35. The extent to which the resilient element 4 received in the adjustment element 3 is compressed or extended is adjusted through forward and rearward displacement of the rear lid 32 or the front lid 35 relative to the cylinder 31, thereby adjusting the magnitude of the resilient force of the resilient element 4.

The present disclosure is disclosed above by preferred embodiments, but the preferred embodiments are not restrictive of the claims of the present disclosure. All equivalent technical changes made to the preferred embodiments in accordance with the accompanying drawings and specification of the present disclosure shall be deemed falling within the claims of the present disclosure.

What is claimed is:

1. A device for alleviating obstructive sleep apnea, comprising:
   a base adapted to be fitted on and fixed to a user's head and the base having a passage portion;
   an adjustment element extending into the passage portion and undergoing relative displacement therein;
   a locking element disposed at the passage portion, wherein the locking element anchors the adjustment element in place to limit relative displacement of the adjustment element;
   a suction member undergoing relative displacement relative to the passage portion and the suction member having a channel, wherein the channel extends into the adjustment element and undergoes relative displacement therein, and further connects to a tongue fixing portion adapted to receive the user's tongue; and
   a negative pressure source in communication with the channel and adapted to provide negative pressure to the tongue fixing portion, wherein the negative pressure source is an electrical module, and the negative pressure source comprises a negative pressure pump and a power source, and the negative pressure source is mounted on the base, wherein the channel is in communication with the negative pressure pump, wherein the negative pressure source comprises a casing with a through hole, and the through hole is centrally disposed in the casing, which is adapted to receive the passage portion.

2. The device for alleviating obstructive sleep apnea according to claim 1, wherein the passage portion extends in a front-rear direction, and the adjustment element undergoes forward and rearward displacement along the passage portion, with the locking element having a locking portion, wherein the locking portion protrudes in a first direction perpendicular to the front-rear direction and is inserted into the passage portion to lock the adjustment element, thereby limiting displacement of the adjustment element in the front-rear direction.

3. The device for alleviating obstructive sleep apnea according to claim 2, wherein an outer surface of the adjustment element is indented inward to form a positioning slot, and the locking portion enters the positioning slot to stop the adjustment element from undergoing displacement in the front-rear direction.

4. The device for alleviating obstructive sleep apnea according to claim 3, wherein the locking element has a retaining portion and a resilient arm, with the retaining portion fixed to the base, wherein the resilient arm is movable relative to the retaining portion in the first direction and has the locking portion.

5. The device for alleviating obstructive sleep apnea according to claim 4, wherein the resilient arm has an unlocking-facilitating portion operating in conjunction with a driving element, wherein one of the unlocking-facilitating portion and the driving element has an unlocking groove, and the other one has an unlocking protruding portion received in the unlocking groove, wherein the driving element has a pressing portion positioned behind the unlocking-facilitating portion and protruding in a direction away from an outer surface of the passage portion, wherein, when the pressing portion is pressed, the driving element drives the locking portion to separate from the positioning slot.

6. The device for alleviating obstructive sleep apnea according to claim 4, wherein the retaining portion comprises a plurality of snap-engagement arms spaced apart from each other and extending forward and rearward, wherein a rear end of each said snap-engagement arm has a snap-engagement bump, allowing the snap-engagement bump and the base to be snap-engaged with each other.

7. The device for alleviating obstructive sleep apnea according to claim 4, wherein the passage portion has a slot receiving the locking element, the slot penetrating the passage portion outward in the first direction and having a limiting segment corresponding in position to the resilient arm, wherein the limiting segment confines the resilient arm to the first direction, and a smallest dimension of the limiting segment in a second direction is less than a largest dimension of the resilient arm in the second direction, wherein the second direction is perpendicular to the first direction and the front-rear direction.

8. The device for alleviating obstructive sleep apnea according to claim 3, wherein the outer surface of the adjustment element and an inner surface of the passage portion have threads operating in conjunction with each other and allowing the adjustment element to rotate and thereby undergo forward and rearward displacement, and the positioning slot is disposed on a threaded area of the outer surface of the adjustment element, wherein the locking portion enters the positioning slot to stop rotation of the adjustment element.

9. The device for alleviating obstructive sleep apnea according to claim 8, wherein the positioning slot extends linearly in the front-rear direction.

10. The device for alleviating obstructive sleep apnea according to claim 1, wherein the suction member has a stopping portion operating in conjunction with the adjustment element and adapted to limit forward displacement of the tongue fixing portion.

11. The device for alleviating obstructive sleep apnea according to claim 10, wherein the suction member has a connector connected to another end of the channel relative to the tongue fixing portion and in communication with the negative pressure source and the channel, wherein the stopping portion is disposed at the connector.

12. The device for alleviating obstructive sleep apnea according to claim 11, wherein the negative pressure source is in communication with the connector via a catheter, and two ends of the connector each have a hermetic seal element, wherein the two hermetic seal elements fit around the channel and the catheter, respectively, to press the channel and the catheter against the connector tightly, wherein the stopping portion is disposed at one of the hermetic seal elements.

13. The device for alleviating obstructive sleep apnea according to claim 12, wherein the connector comprises an axle portion and two mouths disposed at a front end and a rear end of the axle portion, respectively, wherein the hermetic seal elements are connected to the axle portion by the threads, one of the two mouths is inserted into the catheter, and the other one of the two mouths is inserted into the channel, wherein an outer surface of each said mouth has a convex portion protruding outward radially and surrounding the mouth to widen the catheter fitting around one of the two mouths and widen the channel fitting around the other one of the two mouths, wherein any one of the widened catheter and the widened channel is clamped radially by a corresponding one of the convex portions and a corresponding one of the hermetic seal elements.

14. The device for alleviating obstructive sleep apnea according to claim 1, further comprising a resilient element for providing an elastic force under which the tongue fixing portion approaches the base, wherein the elastic force is less than an attractive force adapted to be provided between the suction member and the user's tongue.

15. The device for alleviating obstructive sleep apnea according to claim 14, wherein the adjustment element comprises a front lid, which the suction member abuts against, and a cylinder, the cylinder meshing with the front lid, wherein the resilient element is a spring received in the cylinder, and the resilient element has an end abutting against a rear end of the cylinder and has another end abutting against the suction member, such that the extent to which the resilient element is compressed or extended is adjusted through forward and rearward displacement of the front lid relative to the cylinder.

16. The device for alleviating obstructive sleep apnea according to claim 1, wherein the casing is for receiving the negative pressure pump and the power source.

17. The device for alleviating obstructive sleep apnea according to claim 16, wherein a rail comprising a guiding groove and a fixing recess is concavely disposed on one of an outer surface of the passage portion and an inner surface of the through hole, and the other one of the outer surface of the passage portion and the inner surface of the through hole has a positioning protruding portion operating in conjunction with the rail, wherein the guiding groove extends forward, and the fixing recess extends, such that an included angle is formed between a direction in which the guiding groove extends and a direction in which the fixing recess extends, wherein the passage portion and the casing are combined by moving the positioning protruding portion along the guiding groove and then along the fixing recess before fixing the positioning protruding portion to the fixing recess.

18. The device for alleviating obstructive sleep apnea according to claim 17, wherein the fixing recess comprises a fixing segment extending forward or rearward, and the rail further comprises an engaging member, wherein, when the casing and the base are fixed to each other, the positioning protruding portion is positioned at the fixing segment to block the engaging member and thereby prevent the positioning protruding portion from separating from the fixing recess and consequently entering the guiding groove.

19. The device for alleviating obstructive sleep apnea according to claim 18, further comprising an operating element disposed between the casing and the base to enable the casing to be moved in the front-rear direction relative to the base, thereby allowing the casing to be firmly fixed in place.

20. The device for alleviating obstructive sleep apnea according to claim 19, wherein the operating element is a resilient rubber ring compressed by the casing and the base because of movement of the positioning protruding portion along the guiding groove, wherein, upon admittance of the positioning protruding portion to the fixing recess, both the casing and the base move in the front-rear direction under a resilient force of the operating element, and the positioning protruding portion enters the fixing segment.

21. The device for alleviating obstructive sleep apnea according to claim 18, wherein the casing comprises a front case and a rear case which are combined, and the rail is formed on the front case and the rear case and concavely disposed on an inner surface of the through hole, wherein the fixing segment and the engaging member are disposed on the rear case, and the remainder of the fixing recess is disposed on the front case.

22. The device for alleviating obstructive sleep apnea according to claim 1, wherein the tongue fixing portion is adapted to enclose at least a front end of the user's tongue, and a thickened portion is protrudingly disposed on each of upper and lower outer surfaces of the tongue fixing portion, which is adapted to hold the user's teeth.

23. The device for alleviating obstructive sleep apnea according to claim 22, wherein the thickened portion at the upper outer surface and the thickened portion at the lower outer surface each have an oblique surface, wherein the oblique surface at the upper outer surface and the oblique surface at the lower outer surface approach each other in the upward and downward directions at a front end of the tongue fixing portion, wherein the thickened portions are adapted so that when the user's upper and lower teeth come into contact with the thickened portions, the upper teeth and the lower teeth would approach each other along the oblique surfaces at the upper and lower outer surfaces, and the thickened portions would move rearward relative to the user's teeth, thereby driving the tongue fixing portion and the user's tongue to move rearward relative to the user's teeth.

24. The device for alleviating obstructive sleep apnea according to claim 1, wherein the base comprises a mask portion adapted to allow the user to wear the device, and a gap is disposed between the mask portion and the negative pressure source, wherein the mask portion further has a plurality of ventilation pores in communication with the gap.

25. The device for alleviating obstructive sleep apnea according to claim 1, wherein a negative pressure sensor and a check valve are disposed between the negative pressure pump and the tongue fixing portion, and the check valve is disposed between the negative pressure sensor and the negative pressure pump, wherein the negative pressure sensor measures a magnitude of negative pressure between the check valve and the tongue fixing portion, and the device controls the negative pressure pump according to a measurement, wherein the check valve only permits gas to flow unidirectionally from the tongue fixing portion to the negative pressure pump, such that negative pressure leaking from the negative pressure pump is prevented from transmitting to the negative pressure sensor and the tongue fixing portion.

26. The device for alleviating obstructive sleep apnea according to claim 1, wherein the locking element is a screw, and the base has a threaded hole for meshing with the locking element.

27. The device for alleviating obstructive sleep apnea according to claim 1, wherein the negative pressure source further comprises an active noise-attenuating unit, a negative pressure sensor and a controller, the active noise-attenuating unit attenuating noise generated by the negative pressure pump, the negative pressure sensor monitoring magnitude of negative pressure generated by the negative pressure pump, and the controller starting or shutting down the active noise-attenuating unit and the negative pressure pump simultaneously according to a negative pressure measurement provided by the negative pressure sensor.

28. The device for alleviating obstructive sleep apnea according to claim 27, wherein the active noise-attenuating unit has a built-in noise model corresponding to the negative pressure pump, such that the active noise-attenuating unit generates a first noise-attenuated sound wave with a phase inverse to the built-in noise model when the negative pressure pump starts, wherein after a sound wave resulting from superposition of actual noise generated by the negative pressure pump and the first noise-attenuated sound wave has been received by the active noise-attenuating unit, the active noise-attenuating unit generates a second noise-attenuated sound wave with a phase inverse to the sound wave actually received.

29. The device for alleviating obstructive sleep apnea according to claim 1, wherein the negative pressure source comprises a controller, and the power source is a rechargeable battery, wherein, after receiving a signal which indicates that the power source is being recharged, the controller causes the negative pressure pump to stop functioning.

30. A device for alleviating obstructive sleep apnea, comprising:
    a base adapted to be fitted on and fixed to a user's head and the base having a passage portion;
    an adjustment element extending into the passage portion and undergoing relative displacement therein;
    a suction member undergoing relative displacement relative to the passage portion and the suction member having a channel, wherein the channel extends into the adjustment element and undergoes relative displacement therein, and further connects to a tongue fixing portion adapted to receive the user's tongue; and
    a negative pressure source in communication with the channel and adapted to provide negative pressure to the tongue fixing portion, wherein the negative pressure source comprises a casing with a through hole, and the through hole is centrally disposed in the casing, which is adapted to receive the passage portion.

31. The device for alleviating obstructive sleep apnea according to claim 30, wherein the base further comprises a locking element, and the locking element anchors the adjustment element in place to limit the relative displacement of the adjustment element.

32. The device for alleviating obstructive sleep apnea according to claim 31, wherein the passage portion extends in a front-rear direction, and the adjustment element undergoes forward and rearward displacement along the passage portion, with the locking element having a locking portion, wherein the locking portion protrudes in a first direction perpendicular to the front-rear direction and is inserted into the passage portion to lock the adjustment element, thereby limiting forward and rearward displacement of the adjustment element.

33. The device for alleviating obstructive sleep apnea according to claim 32, wherein an outer surface of the adjustment element is indented inward to form a positioning slot, and the locking portion enters the positioning slot to stop forward and rearward displacement of the adjustment element.

34. The device for alleviating obstructive sleep apnea according to claim 33, wherein the locking element has a retaining portion and a resilient arm, with the retaining portion fixed to the base, wherein the resilient arm is movable relative to the retaining portion in the first direction and has the locking portion.

35. The device for alleviating obstructive sleep apnea according to claim 34, wherein the resilient arm has an unlocking-facilitating portion operating in conjunction with a driving element, wherein one of the unlocking-facilitating portion and the driving element has an unlocking groove, and the other one has an unlocking protruding portion received in the unlocking groove, wherein the driving element has a pressing portion positioned behind the unlocking-facilitating portion and protruding in a direction away from an outer surface of the passage portion, wherein, when the pressing portion is pressed, the driving element drives the locking portion to separate from the positioning slot.

36. The device for alleviating obstructive sleep apnea according to claim 34, wherein the retaining portion comprises a plurality of snap-engagement arms spaced apart from each other and extending forward and rearward, wherein a rear end of each said snap-engagement arm has a snap-engagement bump, allowing the snap-engagement bump and the base to be snap-engaged with each other.

37. The device for alleviating obstructive sleep apnea according to claim 34, wherein the passage portion has a slot receiving the locking element, penetrating the passage portion outward in the first direction, and having a limiting segment corresponding in position to the resilient arm, wherein the limiting segment confines the resilient arm to the first direction, and a smallest dimension of the limiting segment in a second direction is less than a largest dimension of the resilient arm in the second direction, wherein the second direction is perpendicular to the first direction and the front-rear direction.

38. The device for alleviating obstructive sleep apnea according to claim 33, wherein the outer surface of the adjustment element and an inner surface of the passage portion have threads operating in conjunction with each other and allowing the adjustment element to rotate and thereby undergo forward and rearward displacement, and the positioning slot is disposed on a threaded area of the outer surface of the adjustment element.

39. The device for alleviating obstructive sleep apnea according to claim 38, wherein the positioning slot extends linearly in the front-rear direction.

40. The device for alleviating obstructive sleep apnea according to claim 31, wherein the locking element is a screw, and the base has a threaded hole for meshing with the locking element.

41. The device for alleviating obstructive sleep apnea according to claim 30, wherein a positioning protruding portion is protrudingly disposed on an outer surface of the passage portion, wherein a rail is concavely disposed on an inner surface of the through hole and comprises a guiding groove and a fixing recess, the guiding groove extending forward, and the fixing recess extending from the guiding groove in a circumferential direction of the through hole, wherein the passage portion and the casing are combined by moving the positioning protruding portion along the guiding groove and then along the fixing recess before fixing the positioning protruding portion to the fixing recess.

42. The device for alleviating obstructive sleep apnea according to claim 41, wherein the fixing recess has a fixing segment extending rearward, and the positioning protruding portion is positioned at the fixing segment when the casing and the base are fixed to each other.

43. The device for alleviating obstructive sleep apnea according to claim 42, further comprising an operating element disposed between the casing and the base and adapted to move the casing forward relative to the base, thereby allowing the positioning protruding portion to enter the fixing segment.

44. The device for alleviating obstructive sleep apnea according to claim 30, wherein the negative pressure source is mounted on the base, is an electrical module, and comprises a negative pressure pump and a power source, wherein the channel is in communication with the negative pressure pump.

45. The device for alleviating obstructive sleep apnea according to claim 30, wherein the suction member has a stopping portion operating in conjunction with the adjustment element to limit forward displacement of the tongue fixing portion.

46. The device for alleviating obstructive sleep apnea according to claim 30, further comprising a resilient element for providing an elastic force under which the tongue fixing portion approaches the base, wherein the elastic force is less than an attractive force adapted to be provided between the suction member and the user's tongue.

47. The device for alleviating obstructive sleep apnea according to claim 46, wherein the adjustment element comprises a front lid, which the suction member abuts against, and a cylinder, the cylinder meshing with the front lid, wherein the resilient element is a spring received in the cylinder, and the resilient element has an end abutting against a rear end of the cylinder and has another end abutting against the suction member, such that the extent to which the resilient element is compressed or extended is adjusted through forward and rearward displacement of the front lid relative to the cylinder.

* * * * *